(12) United States Patent
Ober et al.

(10) Patent No.: US 8,933,239 B1
(45) Date of Patent: *Jan. 13, 2015

(54) BIS(ARYL)ACETAL COMPOUNDS

(71) Applicant: Dow Global Technologies LLC, Midland, MI (US)

(72) Inventors: Matthias S. Ober, Midland, MI (US); Duane R. Romer, Midland, MI (US); John B. Etienne, Mount Pleasant, MI (US); Pulikkottil J. Thomas, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/943,232

(22) Filed: Jul. 16, 2013

(51) Int. Cl.
*C07F 5/05* (2006.01)
*C07F 5/04* (2006.01)
*C07F 5/02* (2006.01)
*C07C 43/225* (2006.01)

(52) U.S. Cl.
CPC .............. *C07C 43/225* (2013.01); *C07F 5/04* (2013.01); *C07F 5/05* (2013.01); *C07F 5/027* (2013.01); *C07F 5/025* (2013.01)
USPC ........... 548/110; 549/213; 558/287; 558/288; 558/290; 568/3

(58) Field of Classification Search
None
See application file for complete search history.

(56) References Cited

U.S. PATENT DOCUMENTS

| | | |
|---|---|---|
| 2,760,863 A | 8/1956 | Plambeck, Jr. |
| 2,850,445 A | 9/1958 | Oster |
| 2,875,047 A | 2/1959 | Oster |
| 3,097,096 A | 7/1963 | Oster |
| 3,427,161 A | 2/1969 | Laridon et al. |
| 3,479,185 A | 11/1969 | Chambers, Jr. |
| 3,519,605 A | 7/1970 | Takekoshi |
| 3,549,367 A | 12/1970 | Chang et al. |
| 4,189,323 A | 2/1980 | Buhr |
| 4,343,885 A | 8/1982 | Reardon, Jr. |
| 4,442,197 A | 4/1984 | Crivello et al. |
| 4,603,101 A | 7/1986 | Crivello |
| 4,624,912 A | 11/1986 | Zweifel et al. |
| 5,204,442 A | 4/1993 | Nye |
| 5,344,742 A | 9/1994 | Sinta et al. |
| 5,512,207 A | 4/1996 | Manero et al. |
| 5,550,236 A | 8/1996 | Schlosser et al. |
| 5,597,854 A | 1/1997 | Birbaum et al. |
| 5,710,121 A | 1/1998 | Tracy et al. |
| 5,728,835 A | 3/1998 | Aoki et al. |
| 5,837,712 A | 11/1998 | Losel et al. |
| 5,847,149 A | 12/1998 | Fuss et al. |
| 5,919,930 A | 7/1999 | Haber et al. |
| 6,531,291 B1 | 3/2003 | Kabbash et al. |
| 6,670,387 B1 | 12/2003 | Luengo et al. |
| 6,867,250 B1 | 3/2005 | Gupta et al. |
| 7,442,797 B2 | 10/2008 | Itoh et al. |
| 7,632,630 B2 | 12/2009 | Mori et al. |
| 7,892,344 B2 | 2/2011 | Reipen et al. |
| 8,128,848 B2 | 3/2012 | Reipen et al. |
| 8,431,325 B2 | 4/2013 | Hashimoto et al. |
| 8,617,723 B2 | 12/2013 | Stoessel |
| 2002/0099070 A1 | 7/2002 | Agrios |
| 2006/0025548 A1 | 2/2006 | Boussie et al. |
| 2006/0052554 A1 | 3/2006 | Boussie et al. |
| 2006/0199080 A1 | 9/2006 | Amine et al. |
| 2007/0103060 A1 | 5/2007 | Itoh et al. |
| 2009/0137681 A1 | 5/2009 | Sinclair et al. |

(Continued)

FOREIGN PATENT DOCUMENTS

CN  102584741 A  7/2012
DE  19710614 A1  9/1998

(Continued)

OTHER PUBLICATIONS

Urawa et al., "Investigations into the Suzuki-Miyaura coupling aiming at multikilogram synthesis of E2040 using (o-cyanophenyl)boronic esters", Journals of Organometallic Chemistry, vol. 653 (2002), pp. 269-278.

(Continued)

*Primary Examiner* — Alicia L Otton
(74) *Attorney, Agent, or Firm* — Cantor Colburn LLP

(57) ABSTRACT

A bis(aryl)acetal has the formula

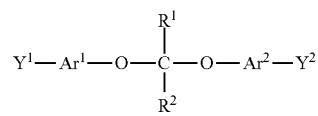

wherein $Y^1$ and $Y^2$ are each independently chloro, bromo, iodo, mesylate, tosylate, triflate, or $B^x$, provided that $Y^1$ and $Y^2$ are not both selected from chloro, bromo, and iodo; each occurrence of $B^x$ is independently a boron-containing functional group bonded to $Ar^1$ or $Ar^2$ via a boron atom; $Ar^1$ and $Ar^2$ are each independently unsubstituted or substituted $C_{6-18}$ arylene, or unsubstituted or substituted $C_{3-18}$ heteroarylene; provided that $Ar^1$ and $Ar^2$ are not covalently linked to each other to form a ring structure that includes

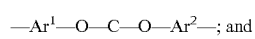

$R^1$ and $R^2$ are each independently hydrogen, unsubstituted or substituted $C_{1-18}$ linear or branched alkyl, unsubstituted or substituted $C_{3-20}$ cycloalkyl, unsubstituted or substituted $C_{6-18}$ aryl, or unsubstituted or substituted $C_{3-20}$ heteroaryl. The bis(aryl)acetal is useful as a monomer for oligoacetal and polyacetal synthesis via Suzuki polycondensation.

10 Claims, No Drawings

(56) References Cited

U.S. PATENT DOCUMENTS

| | | |
|---|---|---|
| 2009/0142681 A1 | 6/2009 | Reipen et al. |
| 2009/0209533 A1 | 8/2009 | Zablocki et al. |
| 2012/0141939 A1 | 6/2012 | Thackeray et al. |

FOREIGN PATENT DOCUMENTS

| | | | |
|---|---|---|---|
| DE | 102008032092 | A1 | 1/2010 |
| EP | 0164248 | A2 | 12/1985 |
| EP | 0232972 | A2 | 8/1987 |
| EP | 0474596 | A1 | 3/1992 |
| JP | 2006008953 | A | 1/2006 |
| JP | 2007284402 | A | 11/2007 |
| JP | 2008110944 | A | 5/2008 |
| JP | 2009209090 | A | 9/2009 |
| WO | 9641166 | | 12/1996 |
| WO | 9713762 | A1 | 4/1997 |
| WO | 9952915 | A1 | 10/1999 |
| WO | 0136386 | A1 | 5/2001 |
| WO | 0142211 | A2 | 6/2001 |
| WO | 0243760 | A1 | 6/2002 |
| WO | 03091262 | A1 | 11/2003 |
| WO | 2007099392 | A2 | 9/2007 |
| WO | 2008014497 | A2 | 1/2008 |
| WO | 2008021048 | A2 | 2/2008 |
| WO | 2008033197 | A2 | 3/2008 |
| WO | 2008070733 | A2 | 6/2008 |
| WO | 2008088690 | A2 | 7/2008 |
| WO | 2009061924 | A2 | 5/2009 |
| WO | 2011116951 | A1 | 9/2011 |
| WO | 2011159633 | A1 | 12/2011 |
| WO | 2011161451 | A1 | 12/2011 |
| WO | 2012004674 | A2 | 1/2012 |
| WO | 2012004675 | A2 | 1/2012 |
| WO | 2012004676 | A2 | 1/2012 |
| WO | 2012004680 | A2 | 1/2012 |
| WO | 2012004681 | A2 | 1/2012 |
| WO | 2012004683 | A2 | 1/2012 |
| WO | 2012006230 | A1 | 1/2012 |

OTHER PUBLICATIONS

Bicerano, J. 2002, "For Tg at infinite molecular weights: Eq. 6.2, 6.3", Prediction of Polymer Properties, Third Edition, Marcel Dekker Inc.: New York, pp. 198-199.

Bicerano, J. 2002, "For Tg at other molecular weights: Eq. 6.4, 6.5, 6.8, 6.10" Prediction of Polymer Properties, Third Edition, Marcel Dekker Inc.: New York, p. 216-217.

Bicerano, J. 2002, "Solubility parameter at 298 K Eq. 5.4" Prediction of Polymer Properties, Third Edition, Marcel Dekker Inc.: New York, p. 137.

Bicerano, J. 2002, "For Tg at other molecular weights: Eq. 6.4, 6.5, 6.8, 6.10" Prediction of Polymer Properties, Third Edition, Marcel Dekker Inc.: New York, p. 212, 2 pages.

Fedors, "A Method for Estimating Both the Solubility Parameters and Molar Volumes of Liquids. * Supplement", Polymer Engineering and Science, Jun. 1974, vol. 14, No. 6, p. 472.

Fedors, "A Method for Estimating Both the Solubility Parameters and Molar Volumes of Liquids", Polymer Engineering and Science, Feb. 1974, vol. 14, No. 2, pp. 147-154.

Frahn et al., "Suzuki Polycondensation: On Catalyst Derived Phosphorus Incorporation and Reproducibiilty of Molecular Weights", Tetrahedron, vol. 53, No. 45, pp. 15459-15467, 1997.

Ito, "Chemical Amplification Resists for Microlithography", Adv Polym Sci (2005) 172: 37-245.

Karakaya et al., "Full coverage of a hydroxy-substituted poly(paraphenylene) with first- and second-generation dendritic wedges having isocyanate focal points", Acta Polymer., 47, pp. 79-84 (1996).

Kozawa et al., "Impact of Nonconstant Diffusion Coefficient on Latent Image Quality in 22 nm Fabrication using Extreme Ultraviolet Lithography", Journal of Photopolymer Science and Technology, 2008, vol. 21, No. 3, pp. 421-427.

Onishi et al., "Acid Catalyzed Resist for KrF Excimer Laser Lithography", Journal of Photopolymer Science and Technology, 4(3), pp. 337-340 (1991).

Sakamoto et al., "Suzuki Polycondencation: Polyarylenes a la carte", Macromolecular Rapid Communications, 2009, vol. 30, pp. 653-687.

Scheler et al., "Synthesis and Properties of Alternating Fluorene-Based Oligomers for Sub-mm Photopatterning", Macromol. Chem. Phys. 2010, 211, pp. 2081-2089.

Schluter et al, "The Tenth Anniversary of Suzuki Polycondensation (SPC)", Journal of Polymer Science, Part A, Polymer Chemistry, 2001, vol. 39, pp. 1533-1556.

Seechurn et al., "Air-Stable Pd(R-allyl)LCI (L=Q-Phos, P(t-Bu)3, etc.) Systems for C-C/N Couplings: Insight into the Structure-Activity Relationship and Catalyst Activation Pathway", J. Org. Chem. 2011, 76, pp. 7918-7932.

U.S. Appl. No. 13/943,007, filed Jul. 16, 2013; Inventors: Matthias S. Ober, Vipul Jain, and John B. Etienne.

U.S. Appl. No. 13/943,169, filed Jul. 7, 2013; Inventors: Matthias S. Ober, Duane R. Romer, John B. Etienne, and Pulikkottil J. Thomas.

U.S. Appl. No. 13/943,196, filed Jul. 16, 2013; Inventor: Matthias S. Ober.

BIS(ARYL)ACETAL COMPOUNDS

FIELD

The present invention relates to bis(aryl)acetals useful in the synthesis of polyacetals.

INTRODUCTION

Polyacetals are known polymers that have some use in microlithography. (As used herein, for brevity the term "acetal" shall be understood to be generic to "acetal" and "ketal", the term "oligoacetal" shall be understood to be generic to "oligoacetal" and "oligoketal", and the term "polyacetal" shall be understood to be generic to "polyacetal" and "polyketal".) The synthesis of polyacetals typically relies on a polycondensation reaction to form acetal moieties during the polymerization reaction. The reactants include free or protected hydroxyl groups that are consumed in the acetal formation, so the resulting polymers typically do not contain free hydroxyl groups or other functional groups that would interfere with or be consumed in typical acetal formation reactions.

There is a need for materials and methods than can be used to synthesize oligoacetals and polyacetals. It would be desirable if the methods were general to the formation of oligoacetals and polyacetals with and without free hydroxyl groups and other functional groups that are incompatible with polycondensation conditions for formation of oligoacetals and polyacetals.

SUMMARY

One embodiment is a bis(aryl)acetal having the formula

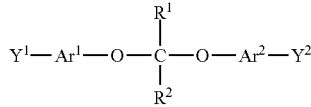

wherein $Y^1$ and $Y^2$ are each independently chloro, bromo, iodo, mesylate, tosylate, triflate, or $B^x$, provided that $Y^1$ and $Y^2$ are not both selected from chloro, bromo, and iodo; each occurrence of $B^x$ is independently a boron-containing functional group bonded to $Ar^1$ or $Ar^2$ via a boron atom; $Ar^1$ and $Ar^2$ are each independently unsubstituted or substituted $C_{6-18}$ arylene, or unsubstituted or substituted $C_{3-18}$ heteroarylene; provided that $Ar^1$ and $Ar^2$ are not covalently linked to each other to form a ring structure that includes

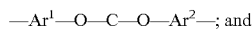; and $R^1$ and $R^2$ are each independently hydrogen, unsubstituted or substituted $C_{1-18}$ linear or branched alkyl, unsubstituted or substituted $C_{3-20}$ cycloalkyl; unsubstituted or substituted $C_{6-18}$ aryl, or unsubstituted or substituted $C_{3-20}$ heteroaryl; and $R^1$ and $R^2$ are optionally covalently linked to each other to form a ring that includes

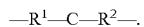.

This and other embodiments are described in detail below.

DETAILED DESCRIPTION

The family of molecules described herein (hereinafter "bis(aryl)acetals") permits the synthesis of oligoacetals and polyacetals having backbone acetal functionality without having to rely on an acetal formation reaction during the last step of the synthesis. Instead, the bis(aryl)acetals serve as the sole monomer or a comonomer in a transition metal catalyzed cross-coupling reaction (e.g., Suzuki coupling). Because of this characteristic, bis(aryl)acetals permit the synthesis of oligomers and polymers with acetal functional groups in the backbone and that can be further substituted with functional groups that are incompatible with many acetal formation reactions—for example, free hydroxyl groups, including free phenols (which would compete in an acetal-forming reaction), and/or acid-labile or base-labile side chains—without having to rely on expensive protection/deprotection strategies.

Oligomers and polymers that contain acetal functional groups in the backbone are useful compounds due to their potential to fragment into smaller molecules upon treatment with Brønsted or Lewis acids or upon electron impact or ionization. Such fragmentation can be used to alter the physicochemical properties (including solubility, aggregate state, glass transition temperature, melting point, and vapor pressure) of materials or formulations comprising the oligomers or polymers. For example, acetal-containing oligomers and polymers are useful in photoresist compositions.

One embodiment is a bis(aryl)acetal having the formula

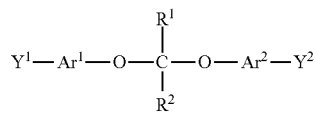

$Y^1$ and $Y^2$ are each independently chloro, bromo, iodo, mesylate, tosylate, triflate, or $B^x$, provided that $Y^1$ and $Y^2$ are not both selected from chloro, bromo, and iodo; each occurrence of $B^x$ is independently a boron-containing functional group bonded to $Ar^1$ or $Ar^2$ via a boron atom; $Ar^1$ and $Ar^2$ are each independently unsubstituted or substituted $C_{6-18}$ arylene, or unsubstituted or substituted $C_{3-18}$ heteroarylene; provided that $Ar^1$ and $Ar^2$ are not covalently linked to each other to form a ring structure that includes —$Ar^1$—O—C—O—$Ar^2$—; and $R^1$ and $R^2$ are each independently hydrogen, unsubstituted or substituted $C_{1-18}$ linear or branched alkyl, unsubstituted or substituted $C_{3-18}$ cycloalkyl; unsubstituted or substituted $C_{6-18}$ aryl, or unsubstituted or substituted $C_{3-18}$ heteroaryl; and $R^1$ and $R^2$ are optionally covalently linked to each other to form a ring that includes —$R^1$—C—$R^2$—. The description of $B^x$ as bonded to $Ar^1$ or $Ar^2$ via a boron atom means that the boron atom is directly covalently bonded to an aromatic carbon of $Ar^1$ or $Ar^2$. The description of $Ar^1$ and $Ar^2$ as not covalently linked to each other to form a ring structure that includes —$Ar^1$—O—C—O—$Ar^2$—means that $Ar^1$ and $Ar^2$ are not directly covalently bonded to each other, nor are they linked via a divalent group that completes a ring also containing —$Ar^1$—O—C—O—$Ar^2$—. The description of $R^1$ and $R^2$ as optionally covalently linked to each other to form a ring that includes —$R^1$—C—$R^2$—means that $R^1$ and $R^2$ can be either directly covalently bonded to each other, or linked via a divalent group that completes a ring also containing —$R^1$—C—$R^2$—.

Also as used herein, "substituted" means including at least one substituent such as a halogen (i.e., F, Cl, Br, I), hydroxyl, amino, thiol, carboxyl, carboxylate, amide, nitrile, sulfide, disulfide, nitro, $C_{1-18}$ alkyl, $C_{1-18}$ alkoxyl, $C_{6-18}$ aryl, $C_{6-18}$ aryloxyl, $C_{7-18}$ alkylaryl, or $C_{7-18}$ alkylaryloxyl. It will be understood that any group or structure disclosed with respect to the formulas herein may be so substituted unless otherwise specified, or where such substitution would significantly adversely affect the desired properties of the resulting structure. Also, "fluorinated" means having one or more fluorine atoms incorporated into the group. For example, where a $C_{1-18}$ fluoroalkyl group is indicated, the fluoroalkyl group can include one or more fluorine atoms, for example, a single fluorine atom, two fluorine atoms (e.g., as a 1,1-difluoroethyl group), three fluorine atoms (e.g., as a 2,2,2-trifluoroethyl group), or fluorine atoms at each free valence of carbon (e.g., as a perfluorinated group such as —$CF_3$, —$C_2F_5$, —$C_3F_7$, or —$C_4F_9$).

In some embodiments of the bis(aryl)acetal formula above, at least one of $Y^1$ and $Y^2$ is $B^x$. In some embodiments, one of $Y^1$ and $Y^2$ is $B^x$, and the other is selected from chloro, bromo, iodo, mesylate, tosylate, and triflate. In such embodiments, the bis(aryl)acetal can be polymerized via Suzuki coupling without the need for a comonomer.

In some embodiments, $Y^1$ and $Y^2$ are each independently selected from mesylate, tosylate, and triflate.

In some embodiments, $Y^1$ and $Y^2$ are each independently $B^x$, wherein each occurrence of $B^x$ is independently selected from the group consisting of —$BF_3^-M^+$, wherein each occurrence of $M^+$ is independently an alkali metal cation, or an unsubstituted or substituted ammonium ion; —$B(OH)_2$;

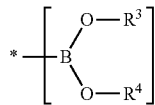

wherein $R^3$ and $R^4$ are each independently $C_{1-18}$ alkyl, $C_{3-18}$ cycloalkyl, or $C_{6-18}$ aryl; and $R^3$ and $R^4$ are optionally covalently linked to each other to form a ring that includes —$R^3$—O—B—O—$R^4$—; and

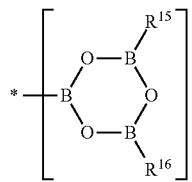

wherein $R^{15}$ and $R^{16}$ are each independently hydrogen, unsubstituted or substituted $C_{1-18}$ linear or branched alkyl, unsubstituted or substituted $C_{3-18}$ cycloalkyl; unsubstituted or substituted $C_{6-18}$ aryl, unsubstituted or substituted $C_{3-18}$ heteroaryl, or

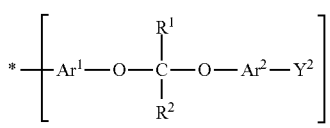

wherein $Y^2$, $Ar^1$, $Ar^2$, $R^1$, and $R^2$ are defined as above.

In some embodiments, each occurrence of $B^x$ is

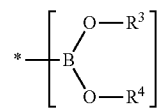

wherein $R^3$ and $R^4$ are each independently $C_{1-18}$ alkyl, $C_{3-18}$ cycloalkyl, or $C_{6-18}$ aryl; and $R^3$ and $R^4$ are optionally covalently linked to each other to form a ring that includes

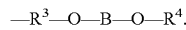

—$R^3$—O—B—O—$R^4$.

Examples of $B^x$ species include

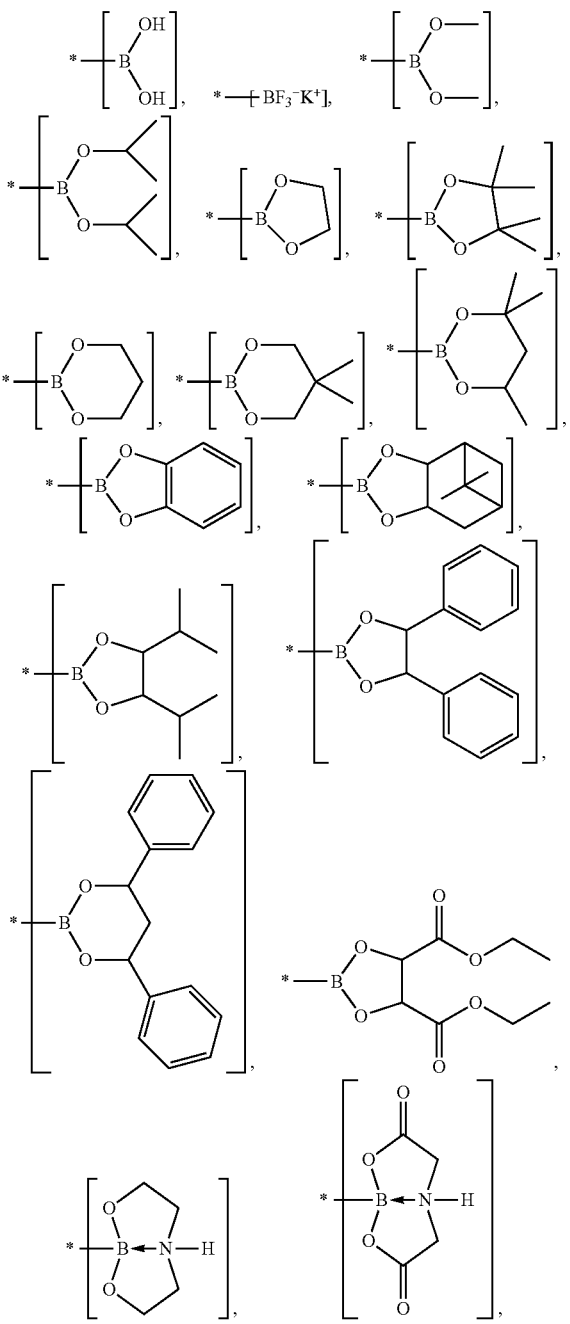

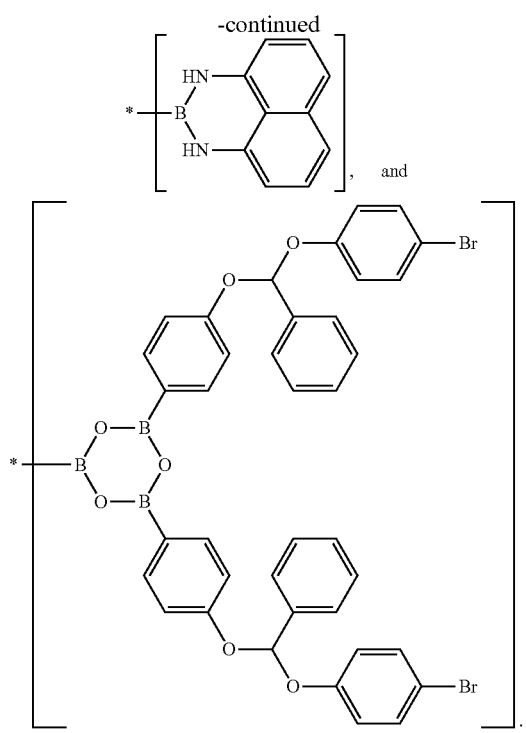

In the bis(aryl)acetal structure above, Ar¹ and Ar² are each independently unsubstituted or substituted $C_{6-18}$ arylene, or unsubstituted or substituted $C_{3-18}$ heteroarylene, provided that Ar¹ and Ar² are not covalently linked to each other to form a ring structure that includes —Ar¹—O—C—O—Ar²—. Specific examples of Ar¹ and Ar² include unsubstituted or substituted 1,2-phenylene, unsubstituted or substituted 1,3-phenylene, unsubstituted or substituted 1,4-phenylene, unsubstituted or substituted 4,4'-biphenylene, unsubstituted or substituted 4,4"-p-terphenylene, unsubstituted or substituted 3,3"-p-terphenylene, unsubstituted or substituted 4,4"-m-terphenylene, unsubstituted or substituted 4,4"-p-terphenylene, unsubstituted or substituted 4,4"-o-terphenylene, unsubstituted or substituted 2,2"-o-terphenylene, unsubstituted or substituted 1,4-naphthylene, unsubstituted or substituted 2,7-naphthylene, unsubstituted or substituted 2,6-naphthylene, unsubstituted or substituted 1,5-naphthylene, unsubstituted or substituted 2,3-naphthylene, unsubstituted or substituted 1,7-naphthylene, unsubstituted or substituted 1,8-naphthylene, unsubstituted or substituted imidazo-2,4-ylene, 2,4-pyridylene, 2,5-pyridylene, unsubstituted or substituted 1,8-anthracenylene, unsubstituted or substituted 9,10-anthracenylene, unsubstituted or substituted 2,7-phenanthrenylene, unsubstituted or substituted 9,10-phenanthrenylene, unsubstituted or substituted 3,6-phenanthrenylene, unsubstituted or substituted 2,7-pyrenylene, unsubstituted or substituted 1,6-pyrenylene, unsubstituted or substituted-1,8-pyrenylene, unsubstituted or substituted 2,5-furanylene, unsubstituted or substituted 3,4-furanylene, unsubstituted or substituted 2,3-furanylene, unsubstituted or substituted 2,5-thiofuranylene, unsubstituted or substituted 3,4-thiofuranylene, unsubstituted or substituted 2,3-thiofuranylene, unsubstituted or substituted 2,5-oxazolylene, unsubstituted or substituted 2,7-fluorenylene, unsubstituted or substituted 2,5-benzofuranylene, unsubstituted or substituted 2,7-benzofuranylene, unsubstituted or substituted 5,7-benzofuranylene, unsubstituted or substituted 5,7-[1,3-benzoxazole], unsubstituted or substituted dithieno[3,2-b:2',3'-d]thiophene, and unsubstituted or substituted 2,7-xanthenylene.

In some embodiments, at least one of Ar¹ and Ar² is substituted with at least one functional group selected from the group consisting of hydroxyl, acetals, ketals, esters, and lactones. The acetals can be monovalent acetals having the structure

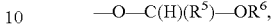

wherein R⁵ and R⁶ are independently selected from the group consisting of unsubstituted or substituted $C_{1-18}$ linear or branched alkyl, unsubstituted or substituted $C_{3-18}$ cycloalkyl, unsubstituted or substituted $C_{6-18}$ aryl, and unsubstituted or substituted $C_{3-18}$ heteroaryl; optionally R⁵ or R⁶ is covalently connected to the polymer backbone such that the acetal is part of a ring structure, provided that the ring structure does not include Ar¹—O—C—O—Ar².

In some embodiments, R⁵ and R⁶ are covalently connected to each others to form a ring structure. Specific examples of monovalent acetals having the structure —O—C(H)(R⁵)—OR⁶ include

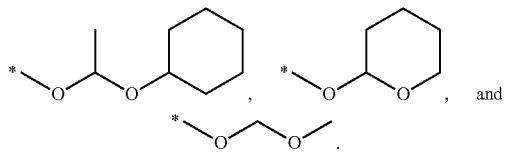

The acetals can also be divalent cyclic acetals attached via oxygen atoms to Ar¹ or Ar² as shown in the structure

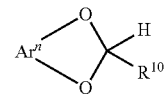

wherein Ar" is Ar¹ or Ar², or a combination of Ar¹ and Ar² (for example, when one acetal oxygen is bonded directly to Ar¹ and the other directly to Ar²); R¹⁰ is selected from the group consisting of unsubstituted or substituted $C_{1-18}$ linear or branched alkyl, unsubstituted or substituted $C_{3-18}$ cycloalkyl, unsubstituted or substituted $C_{6-18}$ aryl, and unsubstituted or substituted $C_{3-18}$ heteroaryl; and O—C(H)(R¹⁰)—O is part of a ring structure provided that the ring structure does not include Ar¹—O—C(R¹)(R²)—O—Ar².

The ketals can be monovalent ketals having the structure

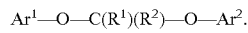

wherein R⁷, R⁸, and R⁹ are independently selected from the group consisting of unsubstituted or substituted $C_{1-18}$ linear or branched alkyl, unsubstituted or substituted $C_{3-18}$ cycloalkyl, unsubstituted or substituted $C_{6-18}$ aryl, and unsubstituted or substituted $C_{3-18}$ heteroaryl; optionally R⁷, R⁸, or R⁹ is covalently connected to the polymer backbone such that the acetal is part of a ring structure, provided that the ring structure does not include Ar¹—O—C—O—Ar².

The ketals can also be cyclic ketals attached via oxygen atoms to $Ar^1$ or $Ar^2$ as shown in the structure

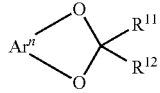

wherein $Ar''$ is $Ar^1$ or $Ar^2$, or a combination of $Ar^1$ and $Ar^2$ (for example, when one ketal oxygen is bonded directly to $Ar^1$ and the other directly to $Ar^2$); $R^{11}$ and $R^{12}$ are independently selected from the group consisting of unsubstituted or substituted $C_{1-18}$ linear or branched alkyl, unsubstituted or substituted $C_{3-18}$ cycloalkyl, unsubstituted or substituted $C_{6-18}$ aryl, and unsubstituted or substituted $C_{3-18}$ heteroaryl; and $O-C(R^{11})(R^{12})-O$ is part of a ring structure provided that the ring structure does not include

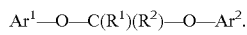

The esters can have the structure

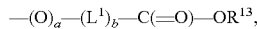

wherein a is 0 or 1 and b is 0 or 1, provided that when a is 1 then b is 1; $R^{13}$ is selected from the group consisting of unsubstituted or substituted $C_{1-20}$ linear or branched alkyl (e.g., methyl, ethyl, n-propyl, i-propyl, n-butyl, i-butyl, t-butyl, diphenylmethyl, 2-phenylpropan-2-yl, 1,1-diphenylethan-1-yl, triphenylmethyl), unsubstituted or substituted $C_{3-20}$ cycloalkyl (e.g., cyclopentyl, cyclohexyl, methylcyclohexan-1-yl, ethylcyclohexan-1-yl, 1-norbornyl, 1-adamantlyl, 2-methylbicyclo[2.2.1]heptan-2-yl, 1-adamantlyl, 2-methyladamantan-2-yl), unsubstituted or substituted $C_{6-20}$ aryl (e.g., phenyl, 1-naphthyl, and 2-naphthyl), and unsubstituted or substituted $C_{3-20}$ heteroaryl (e.g., 2-imidazolyl, 4-imidazolyl, 2-pyridyl, 3-pyridyl, and 4-pyridyl); and wherein $L^1$ is selected from the group consisting of unsubstituted or substituted $C_{1-20}$ linear or branched alkylene (e.g., methane-1,1-diyl ($-CH_2-$), ethane-1,2-diyl ($-CH_2CH_2-$), ethane-1,1-diyl($-CH(CH_3)-$), propane-2,2-diyl($-C(CH_3)_2-$), unsubstituted or substituted $C_{3-20}$ cycloalkylene (e.g., 1,1-cyclopentanediyl, 1,2-cyclopentanediyl, 1,1-cyclohexanediyl, 1,4-cyclohexanediyl), unsubstituted or substituted $C_{6-20}$ arylene (e.g., 1,3-phenylene, 1,4-phenylene, 1,4-naphthylene, 1,5-naphthylene, 2,6-naphthylene), and unsubstituted or substituted $C_{3-20}$ heteroarylene (e.g., imidazo-2,4-ylene, 2,4-pyridylene, 2,5-pyridylene). In some embodiments, $R^{13}$ and $L^1$ are covalently connected to each others to form a lactone. In some embodiments, $R^{13}$ is bonded to the adjacent ester oxygen atom via a tertiary carbon atom, for example,

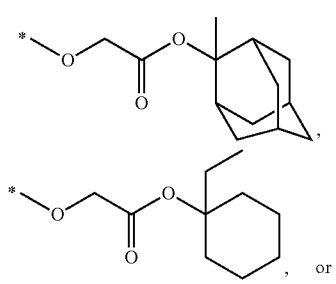

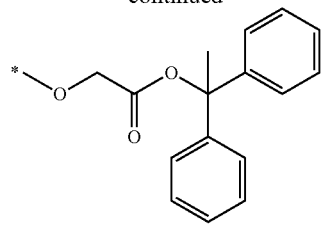

Alternatively, the esters can have the structure

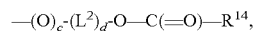

wherein c is 0 or 1 and d is 0 or 1, provided that when c is 1 then d is 1; $R^{14}$ is selected from the group consisting of unsubstituted or substituted $C_{1-20}$ linear or branched alkyl (e.g., methyl, ethyl, n-propyl, i-propyl, n-butyl, i-butyl, t-butyl, diphenylmethyl, 2-phenylpropan-2-yl, 1,1-diphenylethan-1-yl, and triphenylmethyl), unsubstituted or substituted $C_{3-20}$ cycloalkyl (e.g., cyclopentyl, cyclohexyl, 1-norbornyl, 1-adamantlyl, 2-methylbicyclo[2.2.1]heptan-2-yl, 2-methyladamantan-2-yl), unsubstituted or substituted $C_{6-20}$ aryl (e.g., phenyl, 1-naphthyl, 2-naphthyl), and unsubstituted or substituted $C_{3-20}$ heteroaryl (e.g., 2-imidazolyl, 4-imidazolyl, 2-pyridyl, 3-pyridyl, 4-pyridyl); and wherein $L^2$ is selected from the group consisting of unsubstituted or substituted $C_{1-20}$ linear or branched alkylene (e.g., methane-1,1-diyl ($-CH_2-$), ethane-1,2-diyl ($-CH_2CH_2-$), ethane-1,1-diyl ($-CH(CH_3)-$), propane-2,2-diyl ($-C(CH_3)_2-$), 2-methylpropane-1,2-diyl($-CH_2C(CH_3)_2-$), diphenylmethylene ($-C(C_6H_5)_2-$), 1-phenylmethane-1,1-diyl ($-CH(C_6H_5)-$), 2-phenylpropane-1,2-diyl ($-CH_2C(CH_3)(C_6H_5)-$), 1,1-diphenylethane-1,2-diyl ($-CH_2C(C_6H_5)_2-$)), unsubstituted or substituted $C_{3-20}$ cycloalkylene (e.g., 1,1-cyclopentanediyl, 1,2-cyclopentanediyl, 1,1-cyclohexanediyl, 1,4-cyclohexanediyl, ethylcyclohexane-1,4-diyl, 4-methyladamantane-1,4-diyl), unsubstituted or substituted $C_{6-20}$ arylene (e.g., 1,3-phenylene, 1,4-phenylene, 1,4-naphthylene, 1,5-naphthylene, 2,6-naphthylene), and unsubstituted or substituted $C_{3-20}$ heteroarylene (e.g., imidazo-2,4-ylene, 2,4-pyridylene, 2,5-pyridylene). In some embodiments, $R^{14}$ and $L^2$ are covalently connected to each others to form a lactone. A specific example of an ester having the structure $-(O)_c-(L^2)_d-O-C(=O)-R^{14}$ is

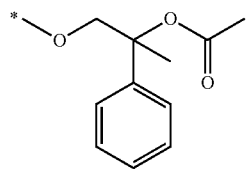

The lactones can have the structure

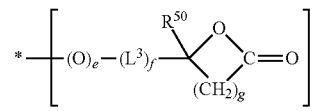

wherein e is 0 or 1; f is 0 or 1; g is 1, 2, 3, or 4 (specifically 2); $R^{50}$ is hydrogen, unsubstituted or substituted $C_{1-18}$ linear or branched alkyl, unsubstituted or substituted $C_{3-18}$ cycloalkyl, unsubstituted or substituted $C_{6-18}$ aryl, or unsubstituted or substituted $C_{3-18}$ heteroaryl; and $L^3$ is selected from the group consisting of unsubstituted or substituted $C_{1-20}$ linear or branched alkylene (e.g., unsubstituted or substituted $C_{3-20}$ cycloalkylene (e.g., 1,1-cyclopentanediyl, 1,2-cyclopentanediyl, 1,1-cyclohexanediyl, 1,4-cyclohexanediyl), unsubstituted or substituted $C_{6-20}$ arylene (e.g., 1,3-phenylene, 1,4-phenylene, 1,4-naphthylene, 1,5-naphthylene, 2,6-naphthylene), and unsubstituted or substituted $C_{3-20}$ heteroarylene (e.g., imidazo-2,4-ylene, 2,4-pyridylene, 2,5-pyridylene).

In some embodiments, at least one of $Ar^1$ and $Ar^2$ is substituted with hydroxyl in at least 40 mole percent of the plurality of repeat units. In other embodiments, each occurrence of $Ar^1$ and $Ar^2$ is independently 1,3-phenylene or 1,4-phenylene.

When used in applications in which the polymer is exposed to acid to promote its fragmentation, it may be desirable for the polymer to exclude robust linkages between the $Ar^1$ and $Ar^2$ rings. Thus, in some embodiments, $Ar^1$ and $Ar^2$ are not covalently linked with one another to form a ring structure that includes —$Ar^1$—O—C—O—$Ar^2$—.

In some embodiments of the bis(aryl)acetal formula above, $Ar^1$ and $Ar^2$ are each independently 1,3-phenylene or 1,4-phenylene, specifically 1,4-phenylene. In other embodiments, at least one of $Ar^1$ and $Ar^2$ is substituted with hydroxyl.

In the bis(aryl)acetal structure above, $R^1$ and $R^2$ are each independently hydrogen, unsubstituted or substituted $C_{1-18}$ linear or branched alkyl (e.g., methyl, ethyl, 1-propyl, 2-propyl, 1-butyl, 2-butyl, 1methyl-2-propyl, diphenylmethyl, 2-phenylpropan-2-yl, 1,1-diphenylethan-1-yl, and triphenylmethyl), unsubstituted or substituted $C_{3-20}$ cycloalkyl (e.g., cyclopentyl, cyclohexyl, 1-norbornyl, 1-adamantlyl, 2-methylbicyclo[2.2.1]heptan-2-yl, 2-methyladamantan-2-yl); unsubstituted or substituted $C_{6-18}$ aryl (e.g., phenyl, 1-naphthyl, 2-naphthyl, anthracenyl), or unsubstituted or substituted $C_{3-18}$ heteroaryl (e.g., 2-imidazolyl, 4-imidazolyl, 2-pyridyl, 3-pyridyl, 4-pyridyl); and $R^1$ and $R^2$ are optionally covalently linked to each other to form a ring that includes —$R^1$—C—$R^2$—. In some embodiments, at least one of $R^1$ and $R^2$ is hydrogen or methyl. In some embodiments, $R^1$ is hydrogen, and $R^2$ is selected from phenyl, ortho-methoxyphenyl, meta-methoxyphenyl, and para-methoxyphenyl. In some embodiments, $R^1$ is hydrogen and $R^2$ is unsubstituted or substituted phenyl. When $R^2$ is substituted phenyl, it can be substituted with a hydroxyl group, an acetal group, an ester group (including a lactone), or other such group that would be incompatible with polyacetal formation via acetal-generating polycondensation or would cause undesired polymer crosslinking. As described in a co-filed application, the present inventors have determined that such groups are tolerated in the Suzuki coupling reaction in which polyacetals are synthesized from the bis(aryl)acetal. Two specific examples of bis(aryl)acetal compounds in which $R^1$ and $R^2$ are covalently linked to each other to form a ring that includes —$R^1$—C—$R^2$— are

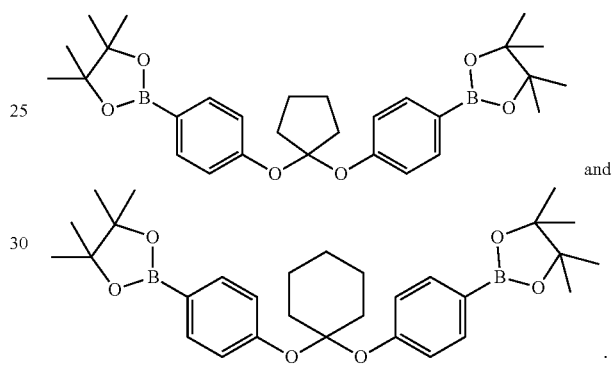

Specific examples of bis(aryl)acetals include

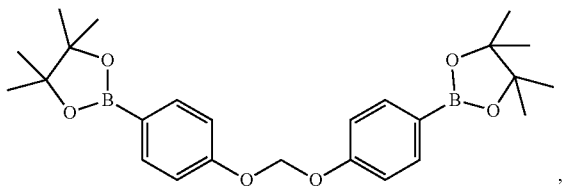 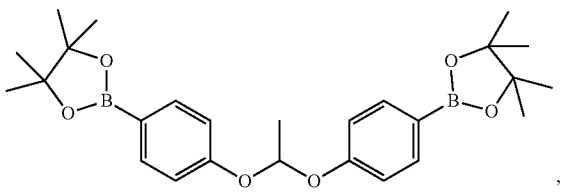

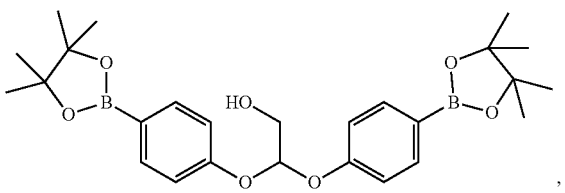 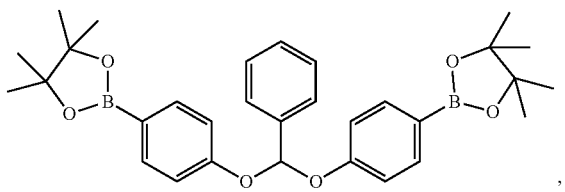

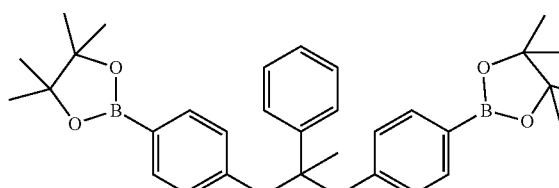 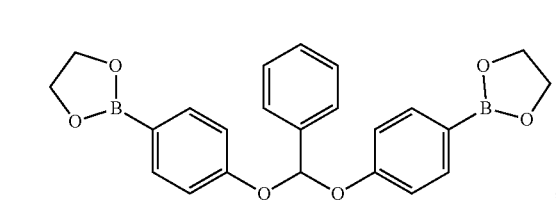

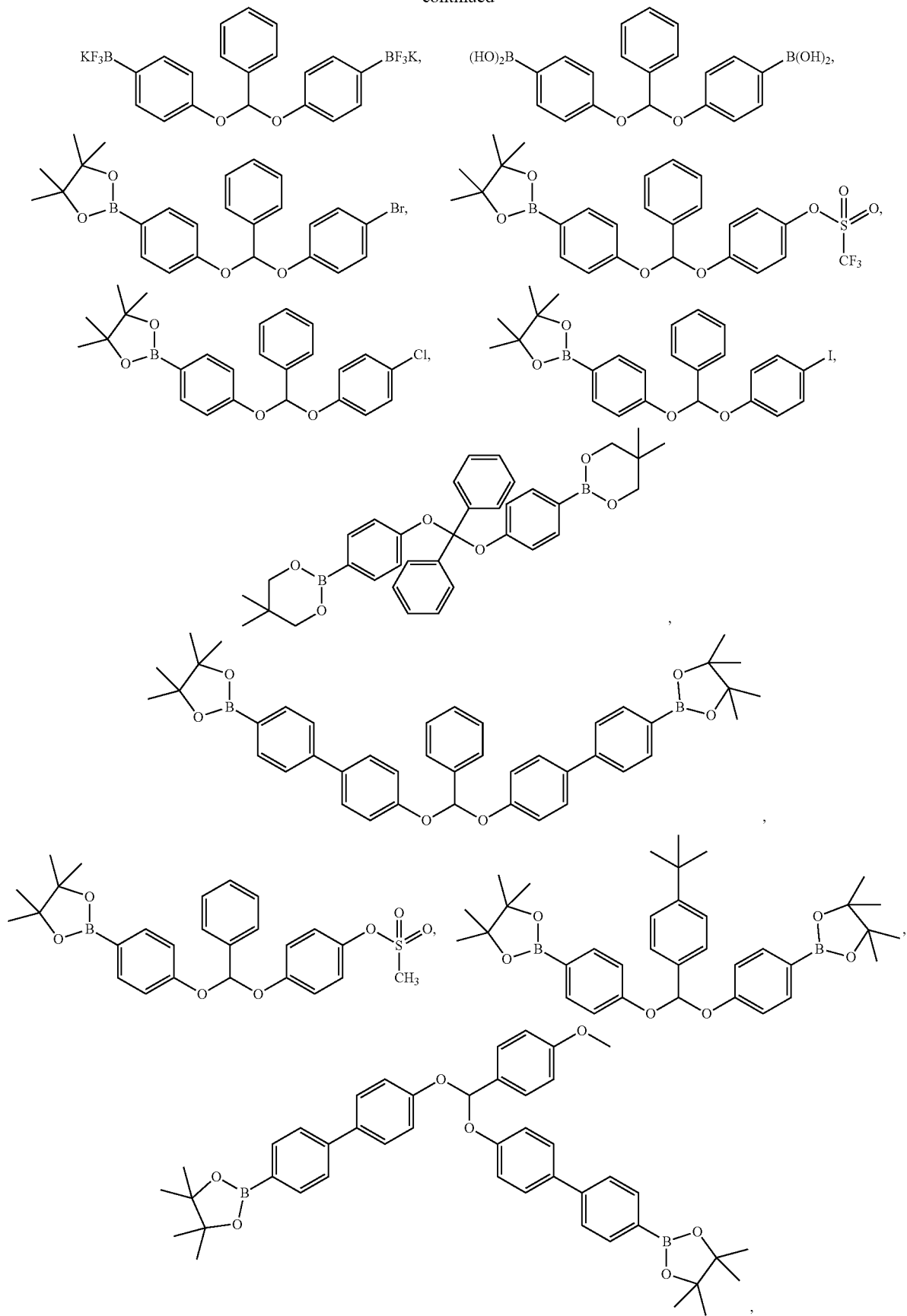

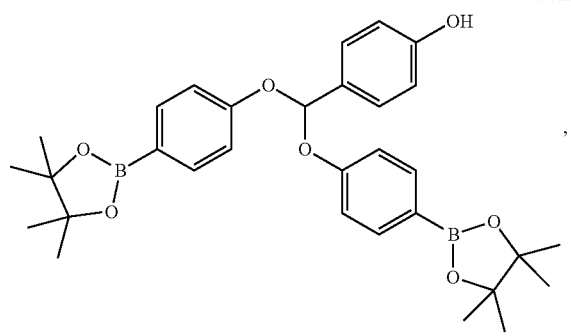
,
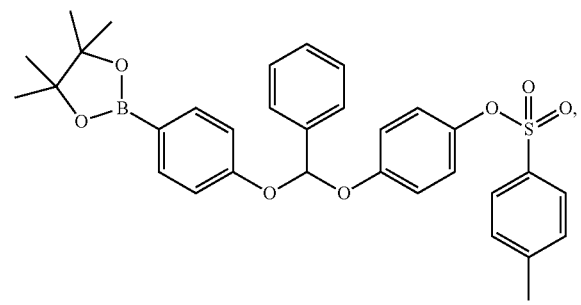
,
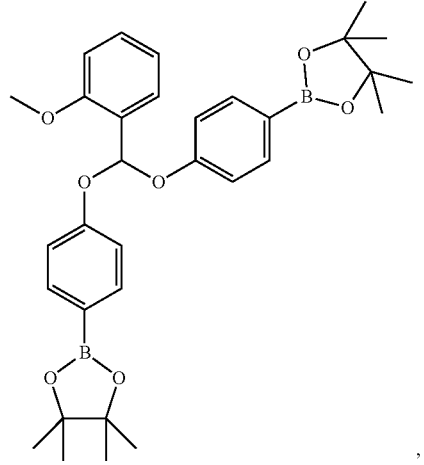
,
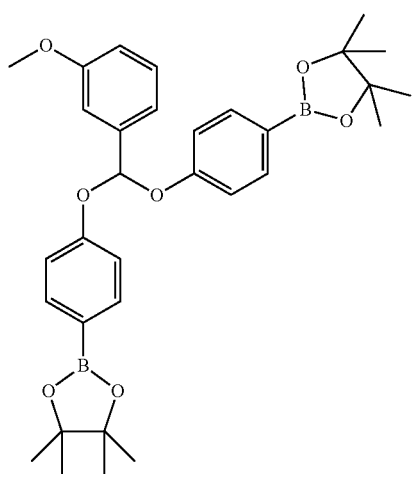
,
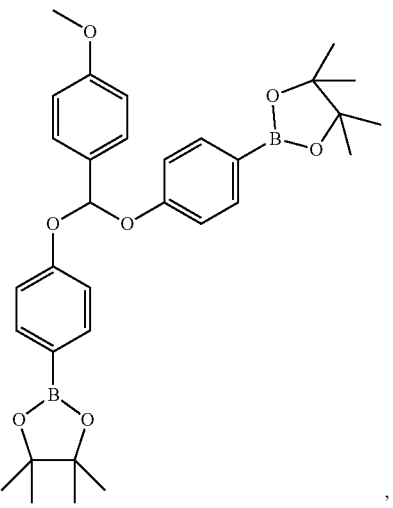
,
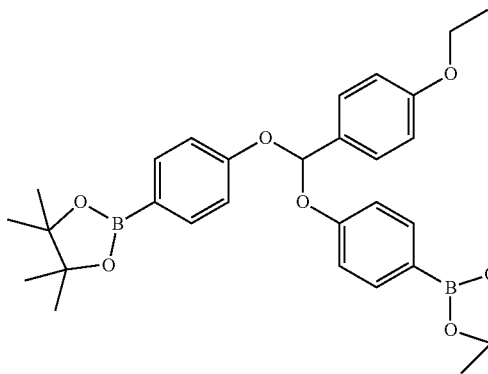
,
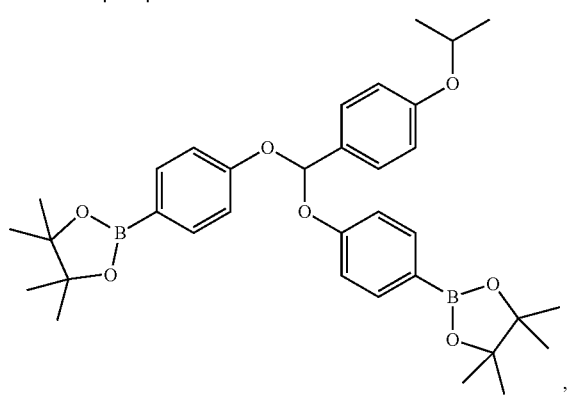
,
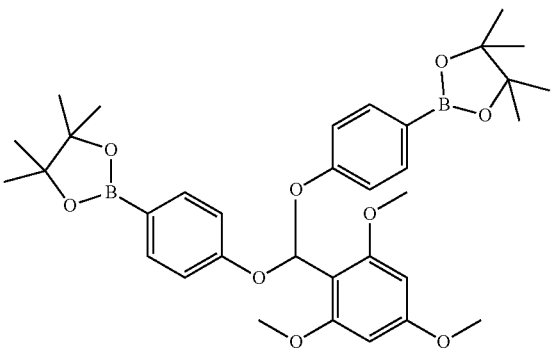
,

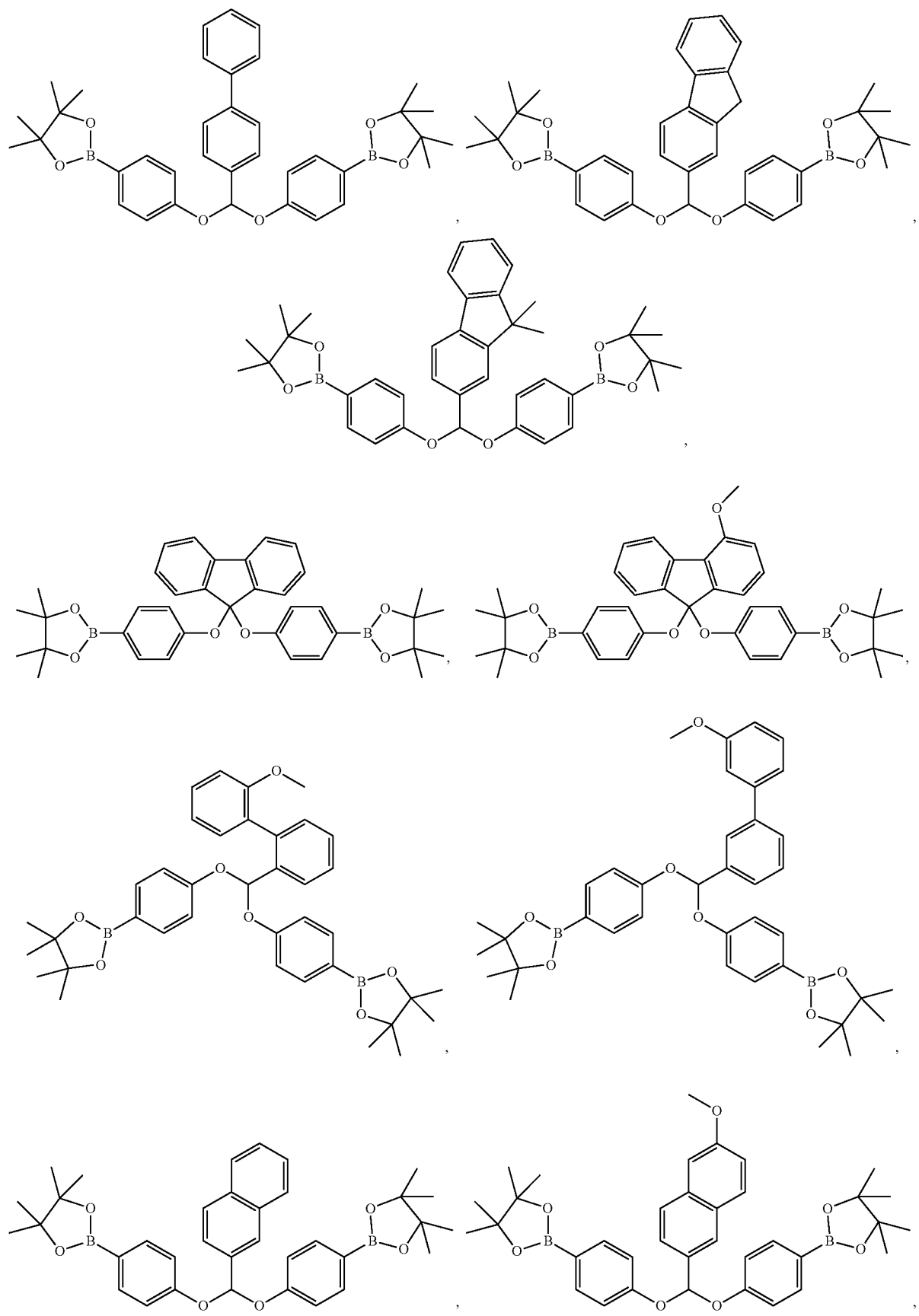

17 18
-continued
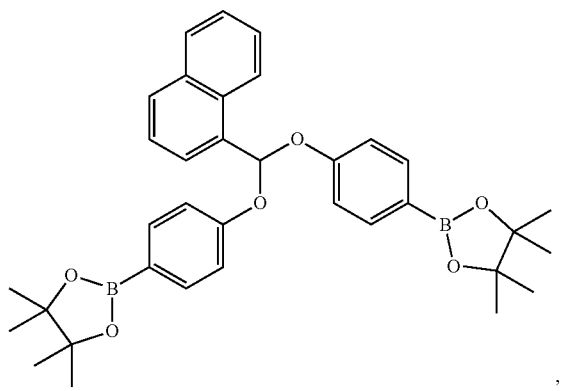
,
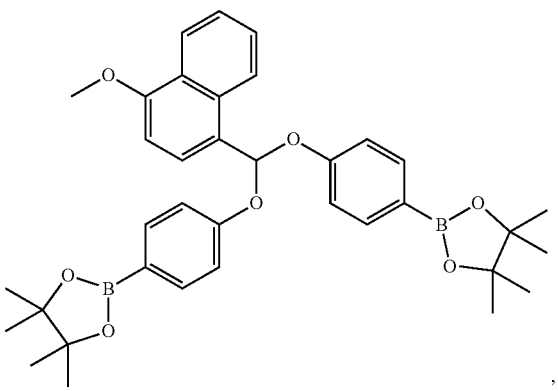
,
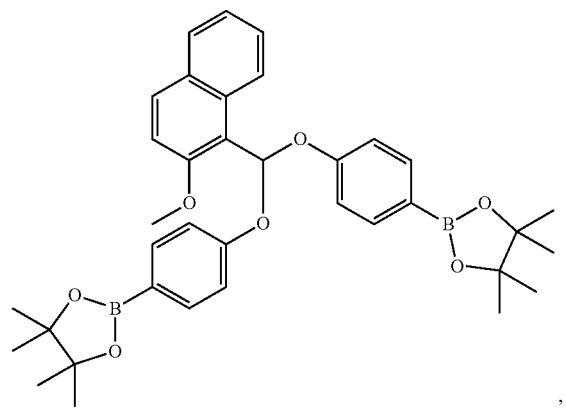
,
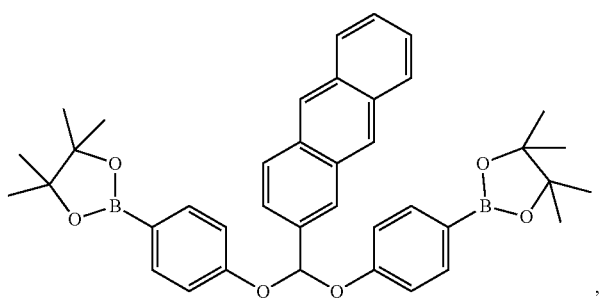
,
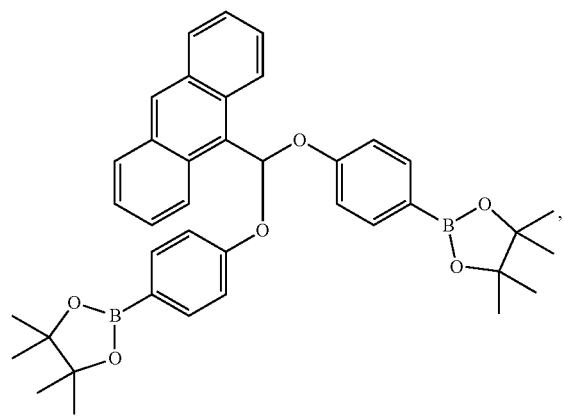
,
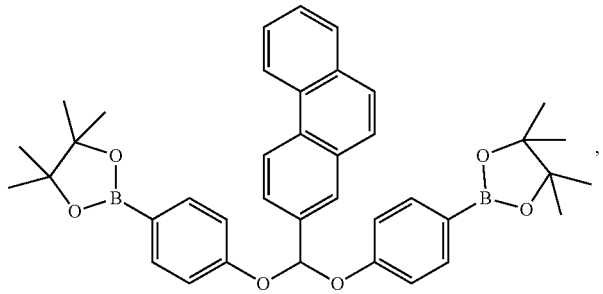
,
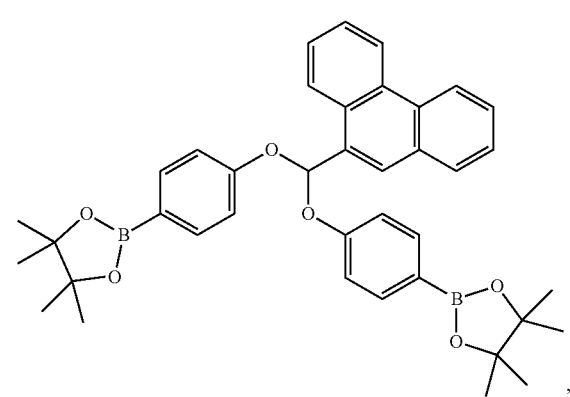
,
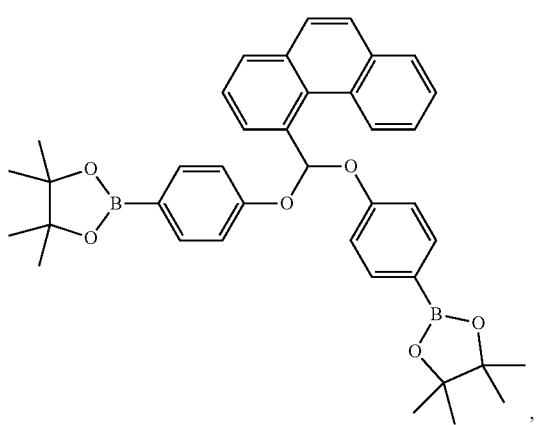
,

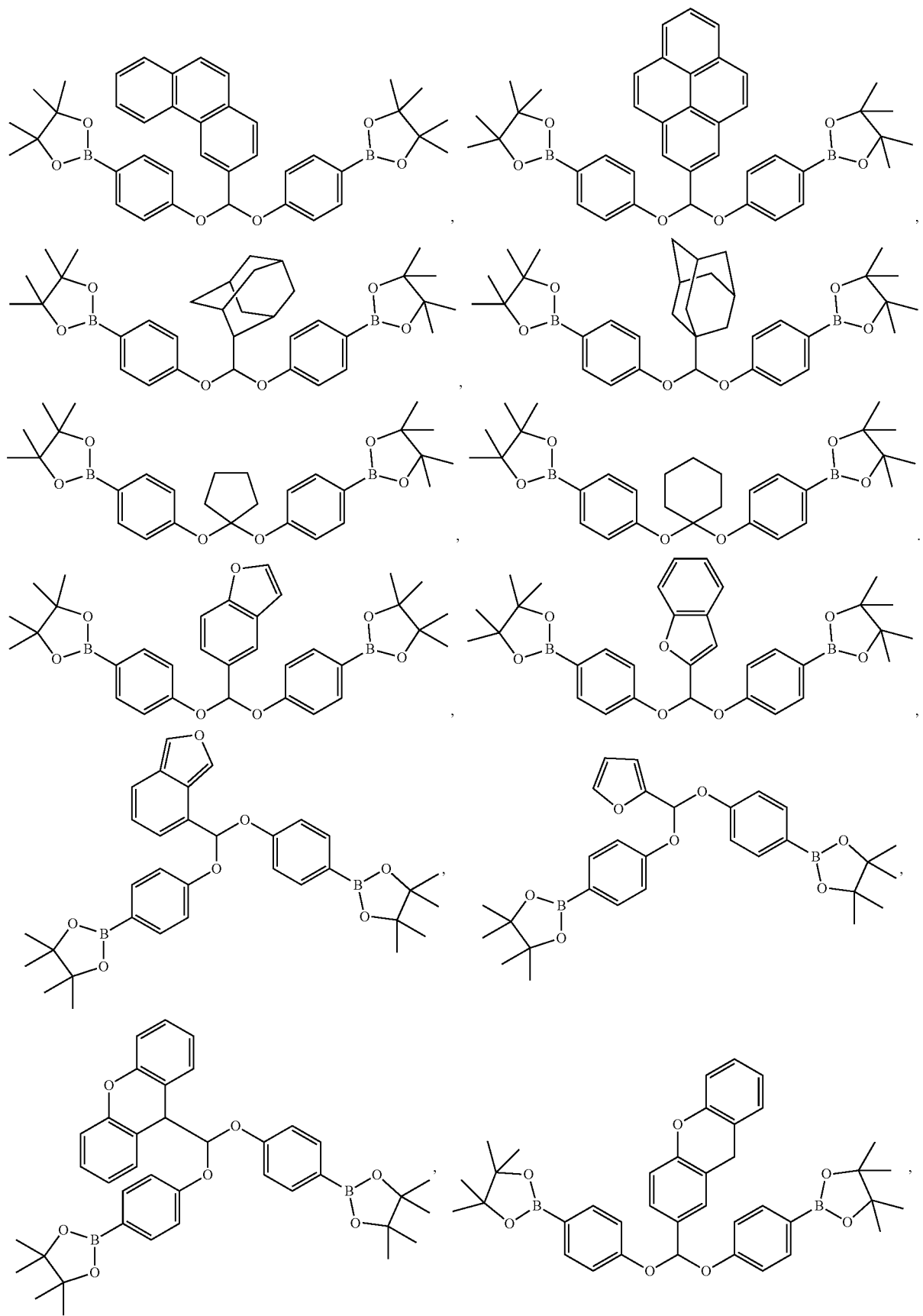

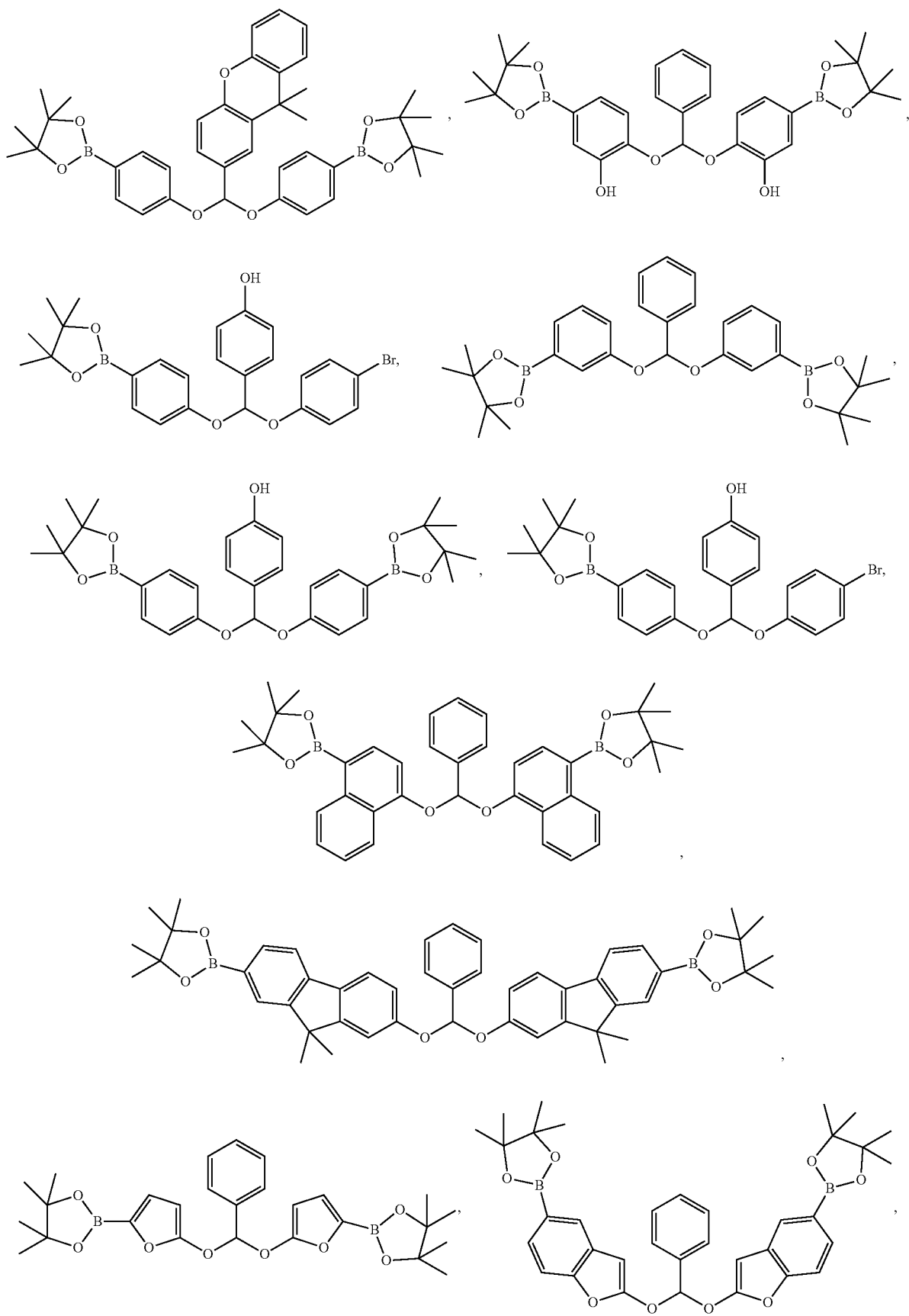

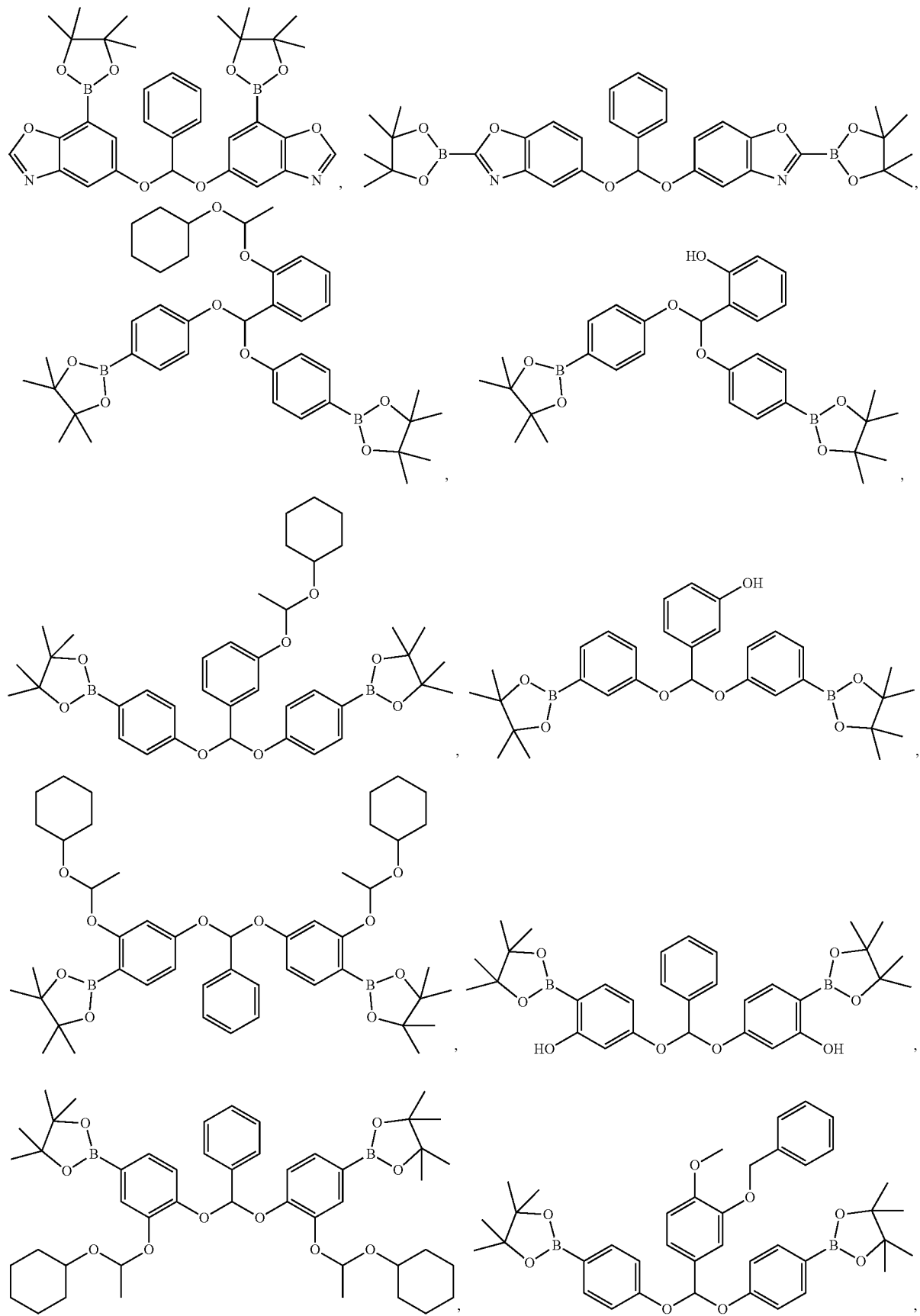

-continued
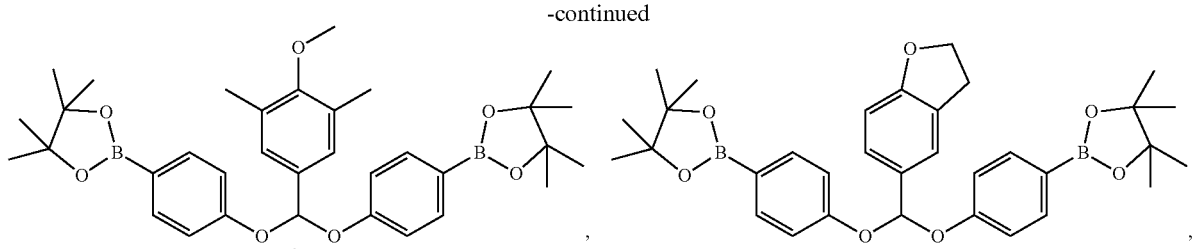
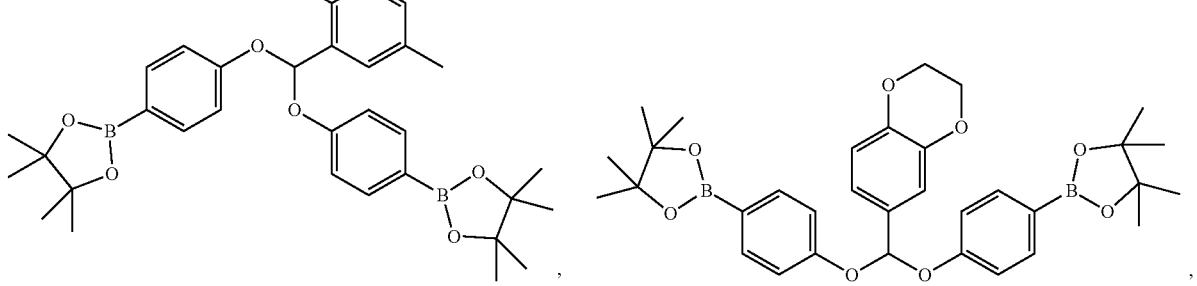
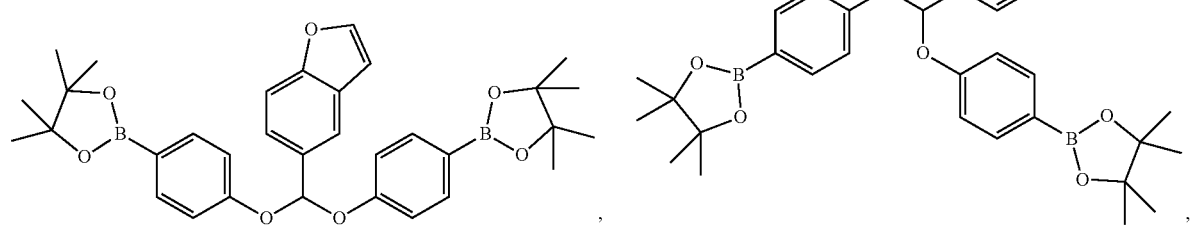
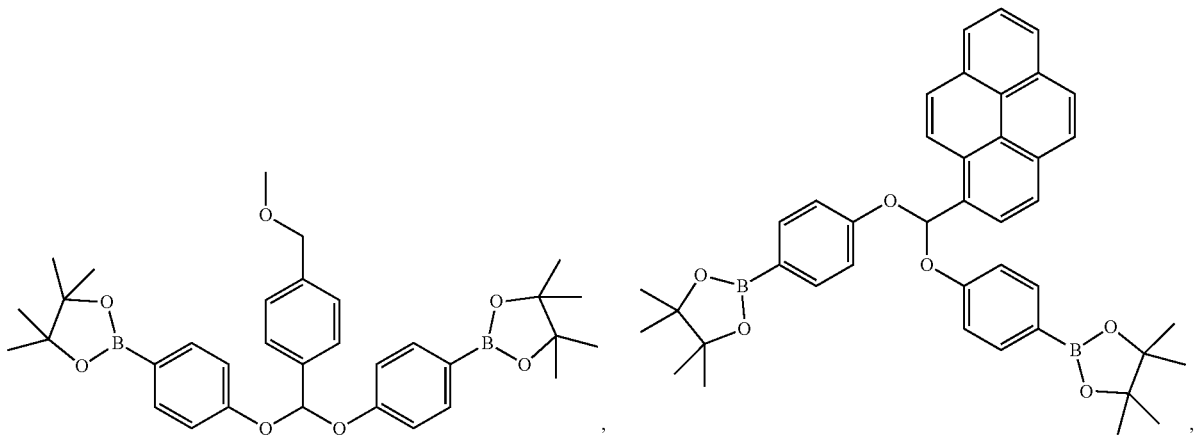
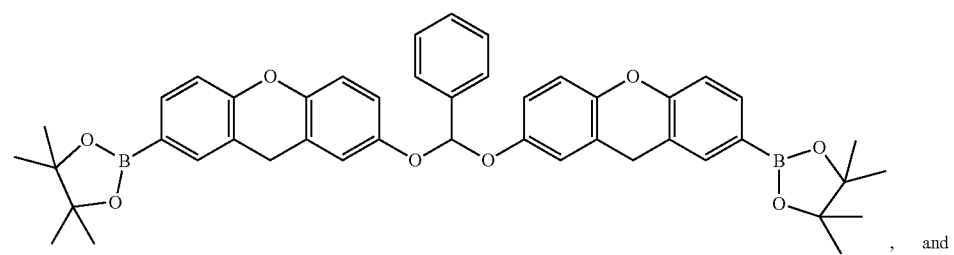
, and

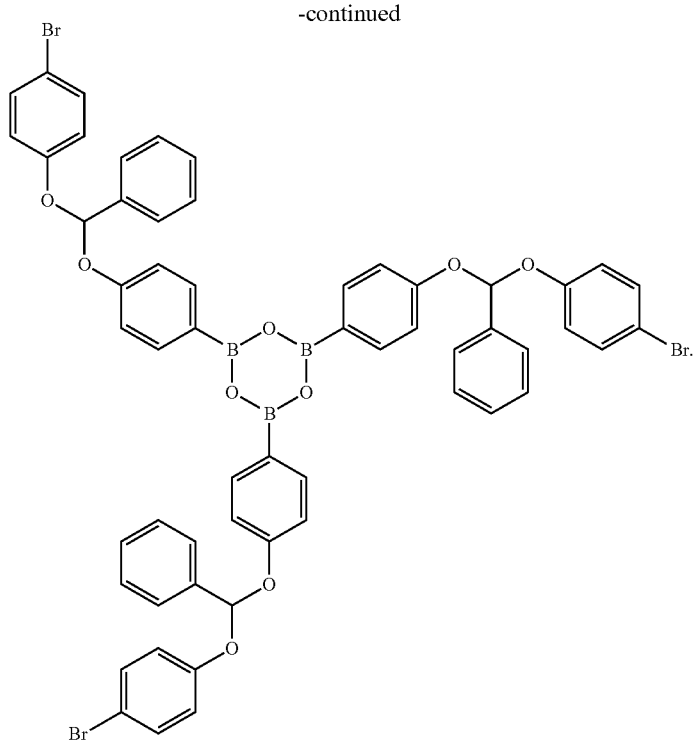

In a very specific embodiment of the bis(aryl)acetal formula above, $Y^1$ and $Y^2$ are each $B^x$; each occurrence of $B^x$ is

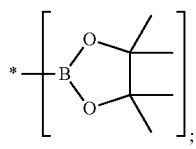

$Ar^1$ and $Ar^2$ are 1,4-phenylene; $R^1$ is hydrogen; and $R^2$ is selected from phenyl, ortho-methoxyphenyl, meta-methoxyphenyl, and para-methoxyphenyl.

Below is an example of a synthesis of a bis(aryl)acetal of the formula above, in which $Y^1$ and $Y^2$ are each independently selected from chloro, bromo, iodo, mesylate, tosylate, and triflate, provided that $Y^1$ and $Y^2$ are not both selected from chloro, bromo, and iodo. Two equivalents of phenol substituted with chloro, bromo, iodo, mesylate, tosylate, or triflate (provided that both equivalents of phenol are not selected from chlorophenol, bromophenol, and iodophenol) are reacted with one equivalent of an $R^1$-substituted 1,1-dihalomethane and two equivalents of sodium hydride to yield the desired product.

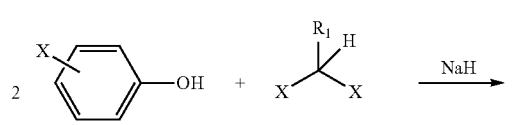

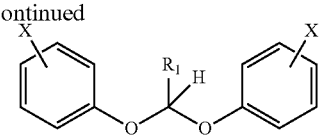

To form a bis(aryl)acetal of the formula above, in which $Y^1$ is $B^x$ and $Y^2$ is selected from chloro, bromo, iodo, mesylate, tosylate, and triflate, the product, a corresponding bis(aryl) acetal in which $Y^1$ and $Y^2$ are each independently selected from chloro, bromo, iodo, mesylate, tosylate, and triflate, can be reacted with one equivalent of butyl lithium followed by one equivalent of a boronic ester, as shown below, to form the desired product. As an alternative to the use of butyl lithium and boronic ester, palladium-catalyzed borylation with bis (picolinato)diboron can be used.

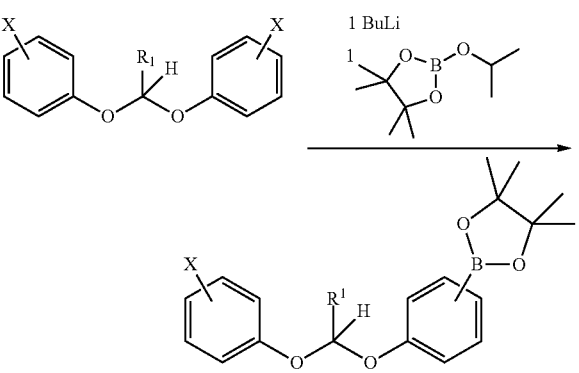

To form a bis(aryl)acetal of the formula above, in which $Y^1$ and $Y^2$ are both $B^x$, the previous reaction is modified to use two equivalents each of butyl lithium followed by two equivalents of boronic ester, as shown below. Again, palladium-catalyzed borylation with bis(picolinato)diboron can be used as an alternative to the use of butyl lithium and boronic ester.

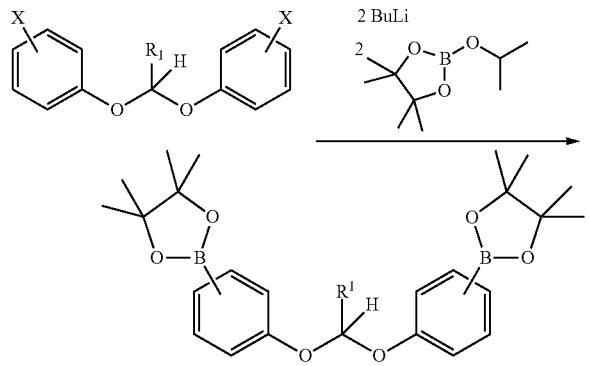

The invention is further illustrated by the following examples.

General Procedures

All solvents and reagents were obtained in commercially available qualities purum, puriss. or p.a. Dry solvents were obtained from in-house purification/dispensing system (hexane, toluene, tetrahydrofuran and diethyl ether) or purchased from Sigma-Aldrich, Fisher Scientific, or Acros. All experiments involving water sensitive compounds were conducted in oven dried glassware under nitrogen atmosphere or in a glovebox. Reactions were monitored by analytical thin-layer chromatography (TLC) on precoated aluminum plates (VWR 60 F254), visualized by UV light and/or potassium permanganate staining. Flash chromatography was performed on an Isco COMBIFLASH™ system with GRACERESOLV™ cartridges.

Proton nuclear magnetic resonance ($^1$H-NMR) spectra (500 megahertz (MHz) or 400 MHz) were obtained on a Varian VNMRS-500 or VNMRS-400 spectrometer at 30° C. unless otherwise noted. The chemical shifts were referenced to tetramethylsilane (TMS) ($\delta$=0.00) in CDCl$_3$, Benzene-d$_5$ (7.15) in Benzene-d$_6$ or tetrahydrofuran-d7 (THF-d$_7$; $\delta$ 3.58 (used) and 1.73) in THF-d$_8$. If necessary, peak assignment was carried out with the help of COSY, HSQC or NOESY experiments. $^{13}$C-NMR spectra (125 MHz or 100 MHz) were obtained on a Varian VNMRS-500 or VNRMS-400 spectrometer, chemical shifts were solvent or standard signals (0.0—TMS in CDCl$_3$, 128.02—Benzene-d$_6$, 67.57 (53.37)— THF-d$_8$). If NMR was used for quantification purposes, single scan experiments or relaxation delays of $\geq$30 seconds were used.

If not otherwise noted, high resolution mass spectrometry was carried out as follows. For ESI/MS and ESI/LC/MS/MS studies, three microliter aliquots of the samples as 1 milligram/milliliter solutions in methanol were injected on an Agilent 1200SL binary gradient liquid chromatograph coupled to an Agilent 6520 QToF, quadrupole-time of flight mass spectrometry system via a dual spray electrospray (ESI) interface operating in the positive ion (PI) mode. The following analysis conditions were used: Column: None—flow injection; Column temperature: 40° C.; Mobile phase: 0.3 M ammonium acetate in methanol; Flow: 0.25 milliliter/min; UV detection: Diode Array 210 to 600 nanometers; ESI conditions: Gas Temp—350° C., Gas Flow—8 milliliters/minute, Capillary—3.5 kilovolt, Nebulizer—45 pounds per square inch, Fragmentor—145 volts; AutoMSMS conditions: Mode—±TOFMS and ±TOFMSMS; Centroid Resolution 12000(+) 2 Ghz Extended Dynamic Range, Scan—100 to 1700 atomic mass units (amu) (±MS), Rate—4 scan/sec, Scan—50 to 1700 atomic mass units (±MS/MS), Rate—4 scans/second, Collision Energy: 5 volts+5 volts/100 atomic mass units, Collision Gas: Nitrogen, Isolation Width about 4 atomic mass units, Reference Ions: 121.050873: 922.009798 (+); 112.985587, 1033.988109.

Infrared spectra were acquired with a Perkin Elmer Spectrum One FT-IR and Universal ATR Sampling Accessory at a nominal resolution of 4 centimeter$^{-1}$ and 16 scans (approximate acquisition time of 90 seconds). The Universal ATR Sampling Accessory was equipped with a single bounce diamond/ZnSe crystal.

Melting points were obtained by differential scanning calorimetry (DSC) measurement in crimped aluminum pans. The samples (about 8 milligrams) were weighed and sealed in an aluminum hermetic (P/N 900793.901 pan and 900794.901 lid) DSC pan and scanned in a TA Instruments Q2000 DSC (Differential Scanning calorimeter) (P/N 970001.901) equipped with an autosampler, nitrogen purge of 50 milliliters/minute and mechanical cooling accessory. The run parameters were 20° C. to 300° C. at 10° C./min. for a single heat. The scans were analyzed using Universal Analysis V4.3A software.

PREPARATIVE EXAMPLE 1

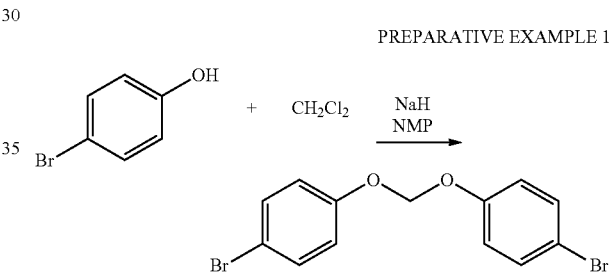

Bis(4-bromophenoxy)methane

To a stirred solution of 4-bromophenol (17.3 grams, 100 millimoles, 1.0 equivalent) in N-methylpyrrolidone (NMP; 120 milliliters) at 0° C. under nitrogen atmosphere was added sodium hydride (NaH; 2.50 grams, 104 millimoles, 1.04 equivalent) in four installments over a period of 1 hour. This solution was stirred for another hour at 0° C. and to this methylene chloride (25 milliliters) was added slowly. After stirring for 1 hour at 0° C., the mixture was warmed to room temperature and then heated to 40° C. for 18 hours. This mixture was poured into cold water (200 milliliters). The mixture was extracted with 5% ethyl acetate in hexanes (3×150 milliliters) and the combined organic layer was washed with water and brine. After drying over anhydrous magnesium sulfate the solvent was removed and the residue was purified by flash chromatography using 10% ethyl acetate in hexanes to yield the product (16.1 grams, 45.0 millimoles, 90%) in the form of a white solid. $^1$H-NMR (CDCl$_3$) $\delta$ 7.40 (dd, J=6.8 Hz and 2.2 Hz, 4H), 6.97 (dd, J=6.8 Hz and 2.2 Hz, 4H) and 5.66 (s, 2H); $^{13}$C-NMR (CDCl$_3$) $\delta$ 155.84, 132.48, 118.28, 115.10, and 91.18.

PREPARATIVE EXAMPLE 2

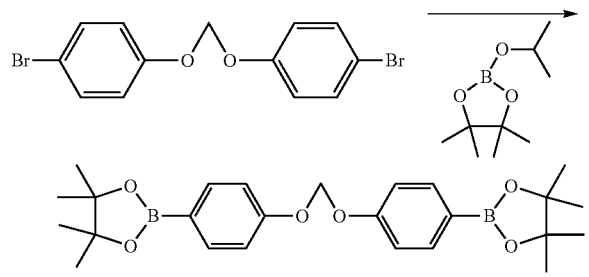

Bis(4-(4,4,5,5-tetramethyl-1,3,2-dioxaborolan-2-yl) phenoxy)methane

To a stirred solution of bis(4-bromophenoxy)methane (4.00 grams, 11.2 millimoles, 1.00 equivalent) in THF (50 mL) at −78° C. under nitrogen atmosphere, n-butyllithium (n-BuLi; 13.6 milliliters, 2.5 M solution in hexane, 33.5 millimoles, 3.00 equivalents) was added slowly. After an hour 2-iso-propoxy-4,4,5,5-tetramethyl-1,3-2-dioxaborolane (6.8 milliliters, 33 millimoles, 3.0 equivalents) was added and stirring was continued at −78° C. for three more hours. The reaction mixture allowed to warm to room temperature and further stirred for 18 hours. The volatiles were removed by rotary evaporation and the residue was treated with crushed ice and extracted with methylene chloride. The organic layer was washed with water and brine, and dried over anhydrous magnesium sulfate. Removal of the solvent followed by recrystallization from pentane gave the diboronate ester (4.11 grams, 9.09 millimoles, 81%) in the form of a white solid. $^1$H-NMR (CDCl$_3$) δ 7.76 (d, J=8.6 Hz, 4H0, 7.08 (d, J=8.6 Hz, 4H), 5.77 (s, 2H) and 1.33 (s, 24H); $^{13}$C-NMR (CDCl$_3$) δ 159.38, 136.53, 115.61, 90.32, 83.62 and 24.83.

PREPARATIVE EXAMPLE 3

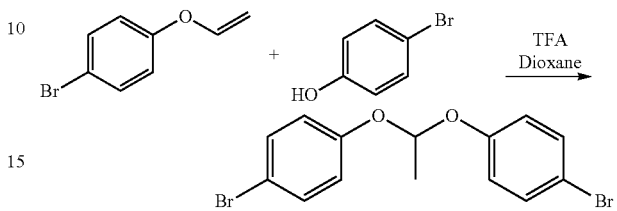

1-Bromo-4-(vinyloxy)benzene

Under nitrogen, a 250 milliliter round bottom flask was charged with 4-bromophenol (8.00 grams, 46.2 millimoles, 1.0 equivalent), sodium acetate (2.28 grams, 27.7 millimoles, 0.6 equivalent) and bis(1,5-cyclooctadiene)diiridium(I) dichloride (233 milligram, 347 micromoles, 0.0075 equivalent). Toluene (75 milliliter) was added to this and vinyl acetate (8.5 milliliter, 92 millimoles, 2.0 equivalents) was added via syringe. The reaction was heated to 102° C. for 3 hours and then allowed to cool to room temperature. The crude reaction was concentrated on a rotary evaporator and filtered through a plug of silica. The solvent was removed by rotary evaporation and the product dried under high vacuum. The final compound was obtained in form of a colorless to slightly yellow oil (6.97 gram, 35.0 millimoles, 76%). $^1$H NMR (500 MHz, CDCl$_3$) δ 7.44-7.37 (m, 2H), 6.91-6.84 (m, 2H), 6.56 (dd, J=13.7, 6.1 Hz, 1H), 4.77 (dd, J=13.7, 1.8 Hz, 1H), 4.45 (dd, J=6.1, 1.8 Hz, 1H).

PREPARATIVE EXAMPLE 4

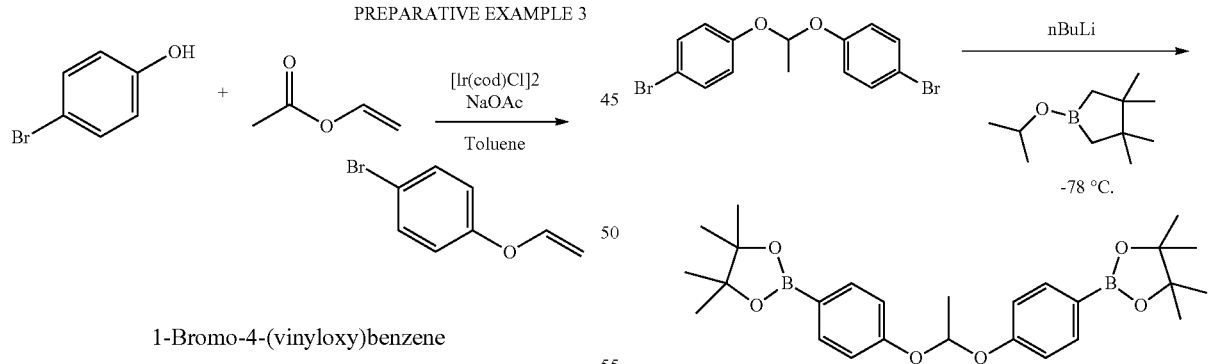

4,4'-(Ethane-1,1-diylbis(oxy)bis(bromobenzene)

Under nitrogen, a 250 milliliter round bottom flask was charged with 1-bromo-4-(vinyloxy)benzene (6.97 grams, 35.0 millimoles, 1.00 equivalent), dioxane (50 milliliters), 4-bromophenol (6.67 grams, 38.5 millimoles, 1.10 equivalent), and a stir bar. Trifluoroacetic acid (1.21 milliliter, 15.75 millimoles, 0.45 equivalent) was added and the flask was equipped with a condenser while maintaining an inert atmosphere. The reaction mixture was heated to reflux overnight, allowed to cool, and quenched with triethylamine (2.00 milliliters). The mixture was separated via automated flash column chromatography using 220 grams Grace normal phase silica column (5% ethyl acetate in hexanes). Concentration gave the product in form of a colorless oil (9.69 grams, 26.0 millimoles, 74%). $^1$H NMR (400 MHz, CDCl$_3$) δ 7.41-7.32 (m, 4H), 6.91-6.81 (m, 4H), 5.86 (q, J=5.3 Hz, 1H), 1.62 (dd, J=5.3, 0.4 Hz, 3H); $^{13}$C-NMR (101 MHz, CDCl$_3$) δ 154.71, 132.46, 119.59, 115.19, 98.44, 20.10.

PREPARATIVE EXAMPLE 5

2,2'-((Ethane-1,1-diylbis(oxy))bis(4,1-phenylene)) bis(4,4,5,5-tetramethyl-1,3,2-dioxaborolane)

Under nitrogen, a 250 milliliter round bottom flask was charged with 4.4-(ethane-1,1-diylbis(oxy)bis(bromobenzene) (9.56 gram, 25.7 millimoles, 1.00 equivalent), tetrahydrofuran (50 milliliters), and a stir bar and cooled to −78° C. in a dry ice/acetone bath. n-Butyllithium (2.5 M in hexane, 25.7 milliliters, 64.2 millimoles, 2.50 equivalents) was added while maintaining an internal temperature between −78 and −70° C. The reaction mixture was then further stirred for one hour at −78° C. Dioxaborolane (15.7 milliliters, 77.1 millimoles, 3.00 equivalents) was added to the solution over a thirty minute period and the reaction mixture was stirred overnight and allowed to gradually warm to ambient temperature. The solution was concentrated, dissolved in ethyl acetate, and filtered through a plug of CELITE™ 545 using ethyl acetate as an eluent. The crude product was concentrated, dissolved in a minimal amount of hot acetonitrile (~150-200 milliliters), filtered hot, and recrystallized by cooling gradually to −20° C. The crystals were isolated by filtration, washed with cold acetonitrile, and dried in a vacuum oven to yield the final product in form of colorless crystalline powder (6.56 grams, 14.7 millimoles, 55%). The mother liquor was concentrated, dissolved a minimum amount of hot acetonitrile. Crystallization at −20° C., followed by isolation by filtration, washing with cold acetonitrile and drying under high vacuum yielded a second crop of product (547 mg) bringing the total yield to 7.10 g (15.2 millimoles, 59%). $^1$H NMR (400 MHz, CDCl$_3$) δ 7.75-7.67 (m, 4H), 6.97-6.89 (m, 4H), 6.05 (q, J=5.2 Hz, 1H), 1.68 (d, J=5.2 Hz, 3H), 1.32 (s, 24H); $^{13}$C NMR (101 MHz, cdcl3) δ 158.50, 136.51, 116.50, 97.43, 83.63, 24.86, 20.42.

PREPARATIVE EXAMPLE 6

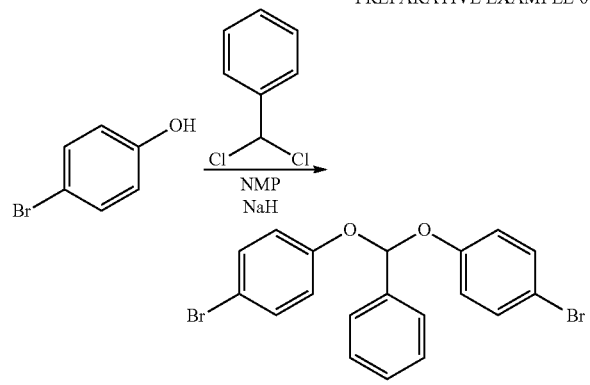

4,4'-((phenylmethylene)bis(oxy))bis(bromobenzene)

Inside a nitrogen purged glove box, to a solution of 4-bromophenol (12.0 grams, 69.4 millimoles, 2.5 equivalents) dissolved in anhydrous 1-methyl-2-pyrrolidinone (100 milliliters), was added 95% sodium hydride (1.82 grams, 72.1 millimoles, 2.6 equivalents) in small portions over a 30 minute period. The reaction was stirred for an additional 90 minutes at room temperature. α,α-Dichlorotoluene (4.13 milliliters, 27.7 millimoles, 1.0 equivalent) was added and the reaction was heated to 70° C. overnight. The reaction was quenched by addition to water (200 milliliters). The aqueous phase was extracted with a 1:1 mixture of diethyl ether and ethyl acetate (3×120 milliliters). The combined organic phases were then washed with de-ionized water (5×100 milliliters), brine (1×100 milliliters) and dried over magnesium sulfate. After filtration and concentration on the rotary evaporator, the residue was taken up in diethyl ether (60 milliliters) and filtered through a plug of basic alumina. The product was fully eluted with additional diethyl ether (700 milliliters) and concentrated on the rotary evaporator. Further drying under high vacuum for several days yielded the product quantitatively in form of a yellow oil that crystallizes over time to give an off-white solid (12.0 grams, 27.7 millimoles, 100%). m.p.: 50.8° C.; $^1$H-NMR (400 MHz, CDCl$_3$) δ 7.59-7.51 (m, 2H), 7.44-7.37 (m, 3H), 7.37-7.29 (m, 4H), 6.93-6.82 (m, 4H), 6.59 (s, 1H); $^{13}$C-NMR (101 MHz, CDCl$_3$) δ 155.07, 136.58, 132.59, 129.65, 128.86, 126.78, 119.60, 115.42, 100.77; FTIR: 605, 658, 674, 694, 741, 792, 816, 848, 886, 928, 984, 1031, 1060, 1100, 1115, 1167, 1178, 1210, 1242, 1280, 1304, 1363, 1449, 1483, 1584, 1689, 3033, 3065 cm$^{-1}$; UV/Vis 223 (shoulder), 237, 278 nm; GC/MS/EI$^+$: 432, 434, 436 [M$^+$] (2×Br isotope pattern); 261, 263 [Br—C$_6$H$_4$—O—CHPh]$^+$ (1×Br isotope pattern); 182 [C$_6$H$_4$—O—CHPh]$^{·+}$ HRMS (ESI): calc. for C$_{19}$H$_{13}$Br$_2$O$_2$ [M+Na]$^+$ 430.9288. found 430.9287.

PREPARATIVE EXAMPLE 6

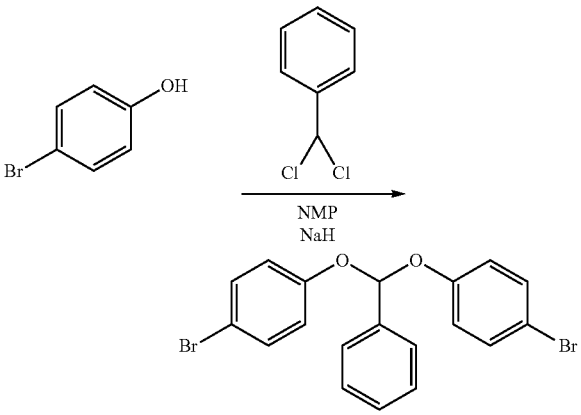

2,2'-(((phenylmethylene)bis(oxy))bis(4,1-phenylene))-bis(4,4,5,5-tetramethyl-1,3,2-dioxaborolane)

4,4'-((phenylmethylene)bis(oxy))bis(bromobenzene) (12.0 grams, 27.6 millimoles, 1.0 equivalent) in anhydrous THF (120 milliliter) under nitrogen was cooled to −78° C. using an acetone/dry ice bath. n-Butyllithium (1.6 M in hexanes, 42 milliliters, 65.5 millimoles, 2.4 equivalents) was added over a 60 minute period. The reaction was stirred at −78° C. for 90 minutes. 2-Isopropoxy-4,4,5,5-tetramethyl-1,3,2-dioxaborolane (17 milliliters, 83.1 millimoles, 3.00 equivalents) was added to the reaction drop-wise over a course of 30 minutes. The reaction was allowed to warm to room temperature overnight. The reaction was carefully quenched by drop-wise addition of water (2 milliliters), followed by stirring for 10 minutes. Dichloromethane (200 milliliters) was added and the reaction mixture was dried over magnesium sulfate. The solids were filtered off and the organic phase was concentrated. The residue was dissolved in dichloromethane (100 milliliters) and filtered through a plug of silica covered with a layer of CELITE™. The produced was fully eluted with additional dichloromethane (400 milliliters) and the combined organic phases concentrated. The plug filtration process was repeated two additional times. After the final concentration, the residue was recrystallized from a minimum amount of boiling acetonitrile that was gradually cooled to 5° C. overnight. The colorless crystals were isolated by filtration, washed with a small aliquot of cold acetonitrile, and dried in under vacuum at 65° C. overnight. The final product was obtained in a yield of 70% (10.2 grams, 19.3 millimoles). $^1$H-NMR (400 MHz, CDCl$_3$) δ 7.72-7.66 (m, 4H), 7.63-7.58 (m, 2H), 7.43-7.35 (m, 3H), 7.00-6.92 (m, 4H), 6.76 (s, 1H), 1.31 (s, 24H); $^{13}$C NMR (101 MHz, cdcl$_3$) δ 158.67, 137.10, 136.46, 129.27, 128.62, 126.69, 116.53, 99.72, 83.63, 24.86, 24.85 (one overlapping peak); FTIR: 578, 632, 651, 697, 733, 756, 832, 855, 884, 919, 964, 996, 1065, 1084, 1096, 1141, 1173, 1210, 1247, 1272, 1322, 1359, 1400, 1458, 1573, 1604, 2927, 2977 cm$^{-1}$; UV/Vis: 242 nm; ESI$^+$: 549, 550, 551, 552, 553 [M+Na]$^+$ (isotope pattern consistent with 2×B and 31×C), 308, 309 (bp), 310 [pinB—C$_6$H$_4$—O—CHPh]$^+$ (isotope pattern consistent with B and 19×C); HRMS (ESI$^+$): calc. for C$_{31}$H$_{38}$B$_2$NaO$_6$$^+$ [M+Na]$^+$ 551.2752. found 551.2762.

The invention claimed is:

1. A bis(aryl)acetal having the formula

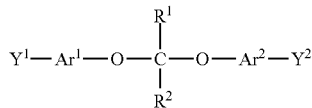

wherein

Y$^1$ and Y$^2$ are each independently chloro, bromo, iodo, mesylate, tosylate, triflate, or B$^x$, provided that Y$^1$ and Y$^2$ are not both selected from chloro, bromo, and iodo;

each occurrence of B$^x$ is independently a boron-containing functional group bonded to Ar$^1$ or Ar$^2$ via a boron atom;

Ar$^1$ and Ar$^2$ are each independently unsubstituted or substituted C$_{6-18}$ arylene, or unsubstituted or substituted C$_{3-18}$ heteroarylene; provided that Ar$^1$ and Ar$^2$ are not covalently linked to each other to form a ring structure that includes

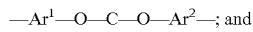

R$^1$ and R$^2$ are each independently hydrogen, unsubstituted or substituted C$_{1-18}$ linear or branched alkyl, unsubstituted or substituted C$_{3-20}$ cycloalkyl; unsubstituted or substituted C$_{6-18}$ aryl, or unsubstituted or substituted C$_{3-20}$ heteroaryl; and R$^1$ and R$^2$ are optionally covalently linked to each other to form a ring that includes

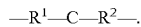

2. The bis(aryl)acetal of claim 1, wherein at least one of Y$^1$ and Y$^2$ is B$^x$.

3. The bis(aryl)acetal of claim 1, wherein Y$^1$ and Y$^2$ are each independently B$^x$.

4. The bis(aryl)acetal of claim 1, wherein each occurrence of B$^x$ is independently selected from the group consisting of —BF$_3$$^-$M$^+$, wherein each occurrence of M$^+$ is independently an alkali metal cation, or an unsubstituted or substituted ammonium ion; —B(OH)$_2$;

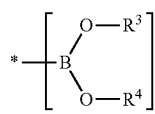

wherein R$^3$ and R$^4$ are each independently C$_{1-18}$ alkyl, C$_{3-18}$ cycloalkyl, or C$_{6-18}$ aryl; and R$^3$ and R$^4$ are optionally covalently linked to each other to form a ring that includes R$^3$—O—B—O—R$^4$; and

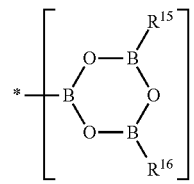

wherein R$^{15}$ and R$^{16}$ are each independently hydrogen, unsubstituted or substituted C$_{1-18}$ linear or branched alkyl, unsubstituted or substituted C$_{3-18}$ cycloalkyl; unsubstituted or substituted C$_{6-18}$ aryl, unsubstituted or substituted C$_{3-18}$ heteroaryl, or

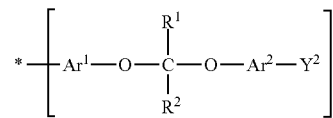

wherein Y$^2$, Ar$^1$, Ar$^2$, R$^1$, and R$^2$ are defined as in claim 1.

5. The bis(aryl)acetal of claim 1, wherein each occurrence of B$^x$ is

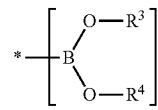

wherein R$^3$ and R$^4$ are each independently C$_{1-18}$ alkyl, C$_{3-18}$ cycloalkyl, or C$_{6-18}$ aryl; and R$^3$ and R$^4$ are optionally covalently linked to each other to form a ring that includes R$^3$—O—B—O—R$^4$.

6. The bis(aryl)acetal of claim 1, wherein Ar$^1$ and Ar$^2$ are each independently 1,3-phenylene or 1,4-phenylene.

7. The bis(aryl)acetal of claim 1, wherein Ar$^1$ and Ar$^2$ are each independently 1,4-phenylene.

8. The bis(aryl)acetal of claim 1, wherein

R$^1$ is hydrogen; and

R$^2$ is unsubstituted or substituted phenyl.

9. The bis(aryl)acetal of claim 1, wherein

R$^1$ is hydrogen; and

R$^2$ is selected from phenyl, ortho-methoxyphenyl, meta-methoxyphenyl, and para-methoxyphenyl.

10. The bis(aryl)acetal of claim 1, selected from the group consisting of

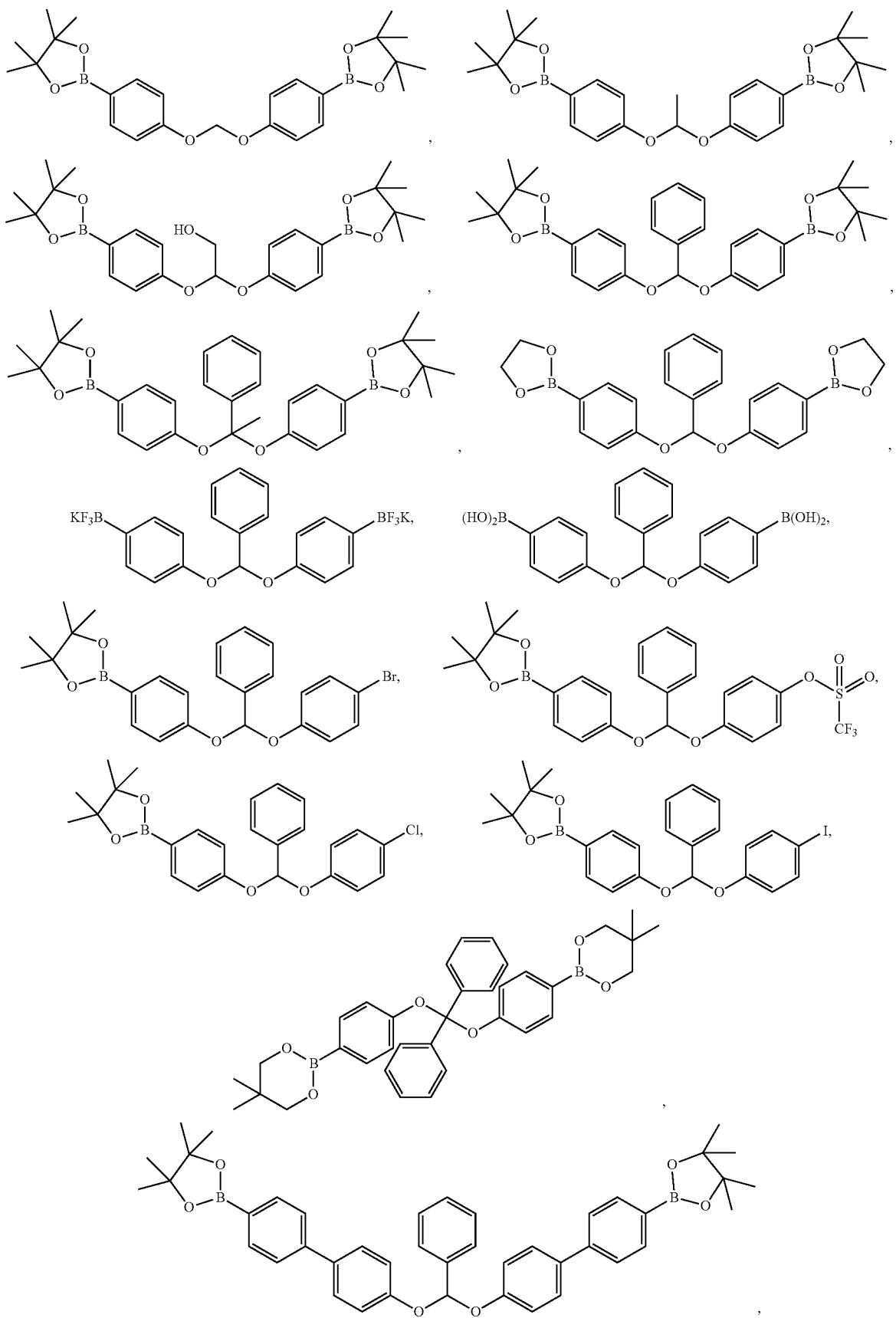

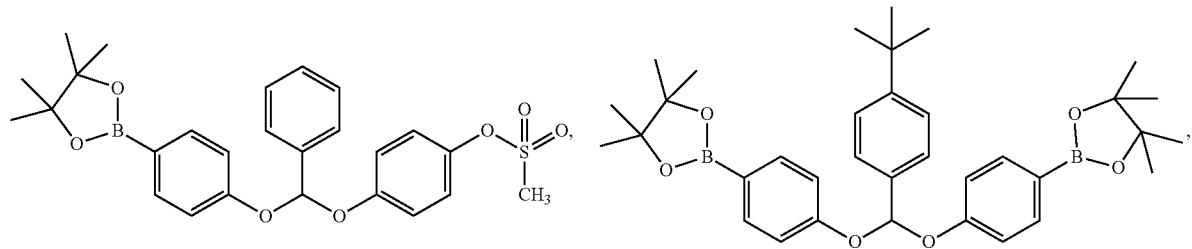
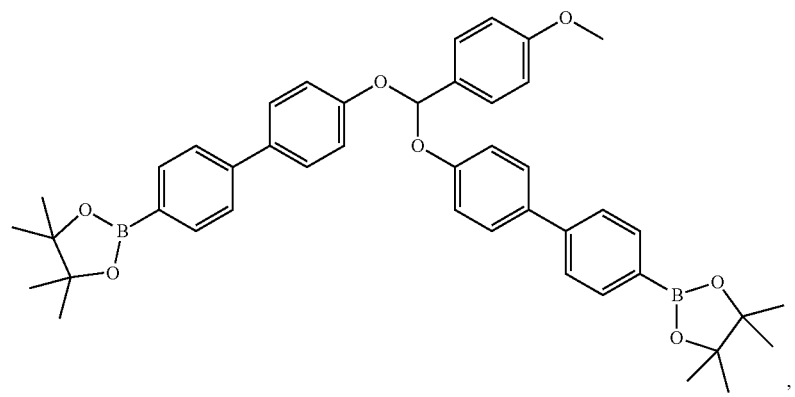
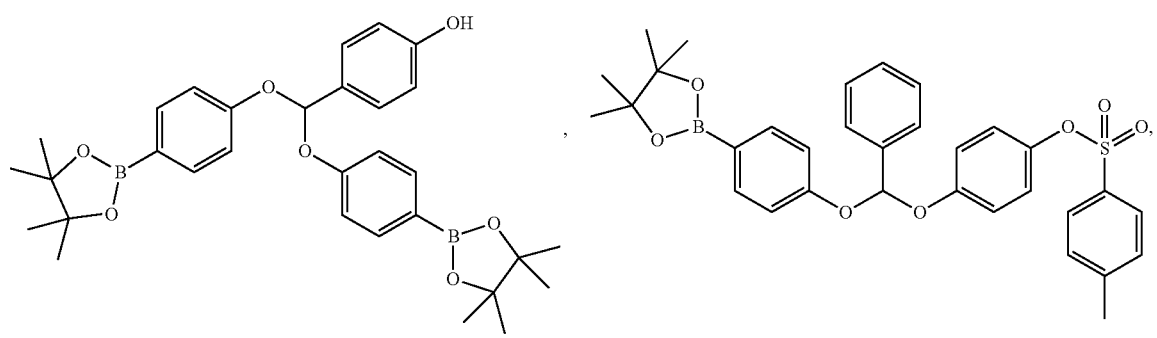
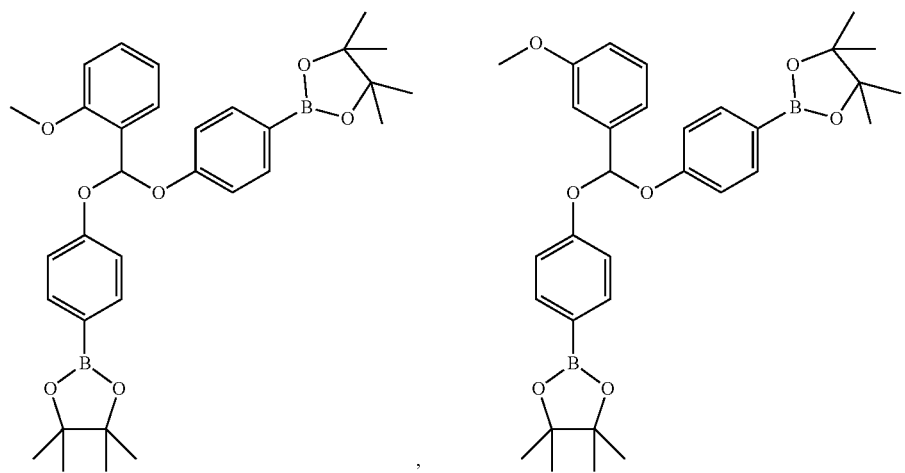

-continued
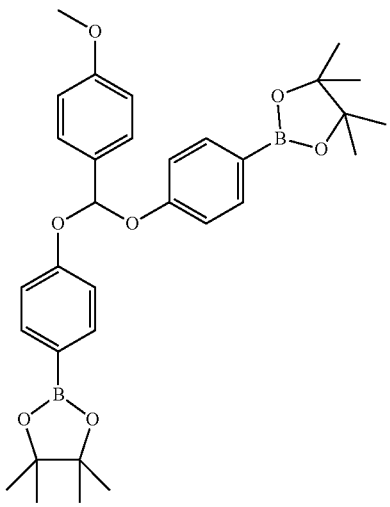
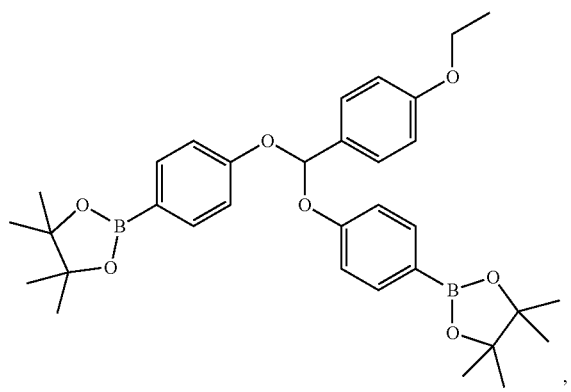
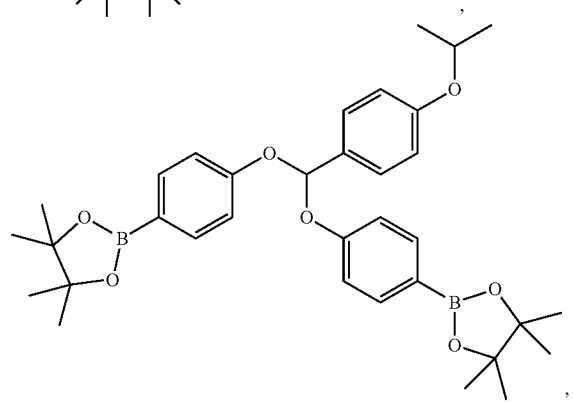
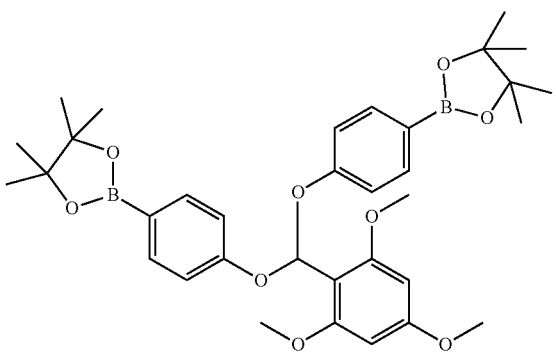
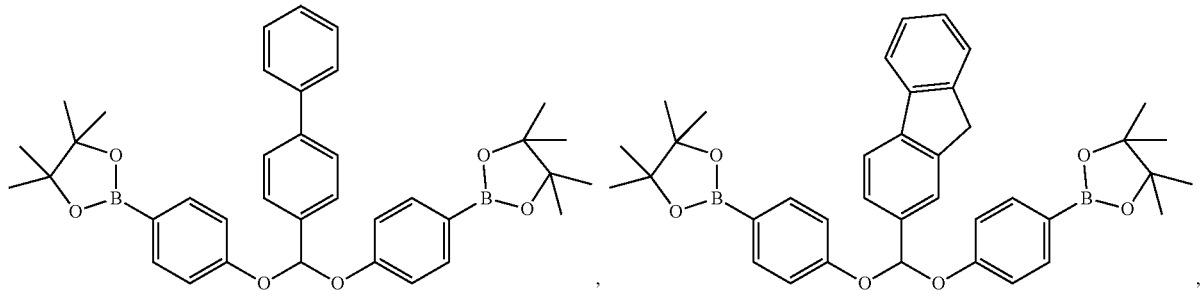
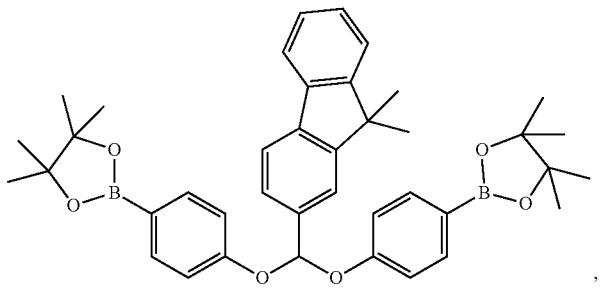
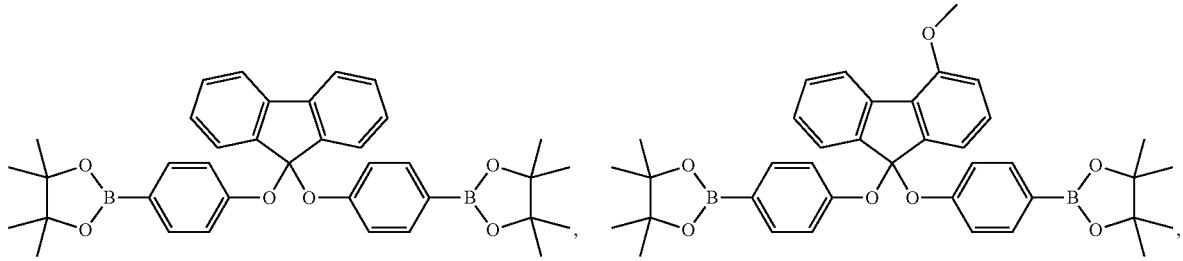

-continued
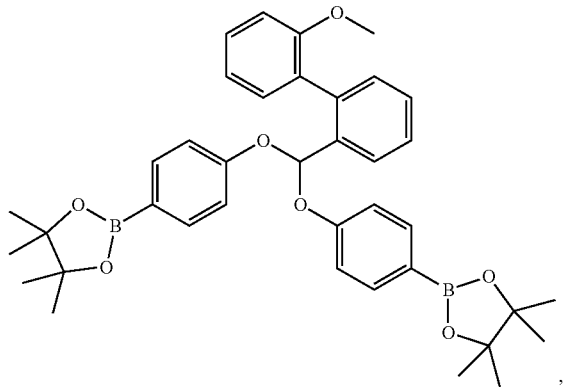
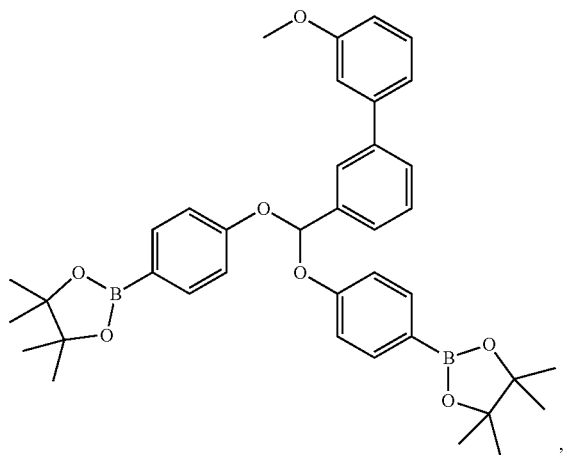
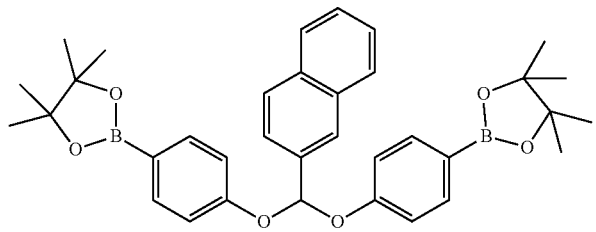
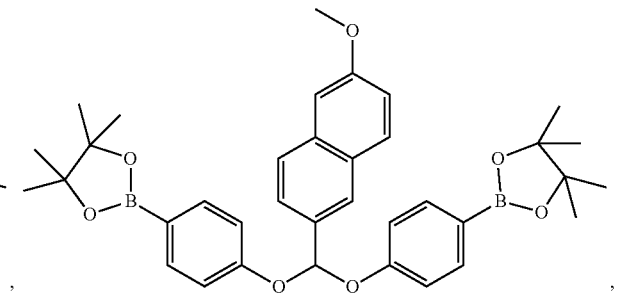
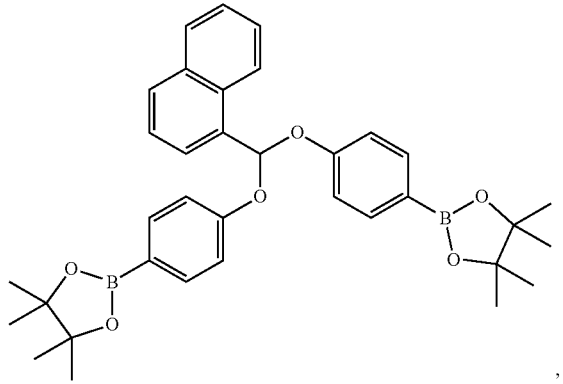
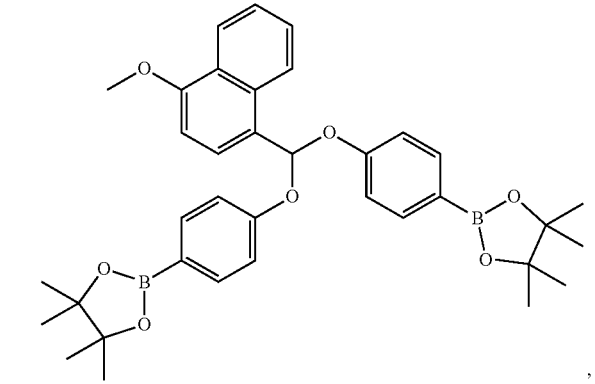
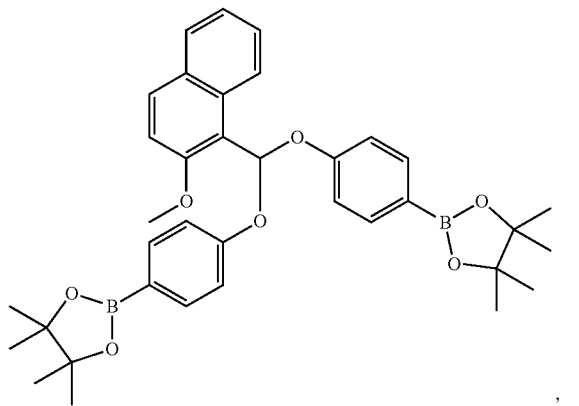
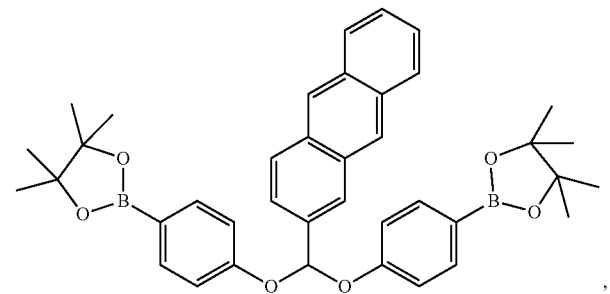

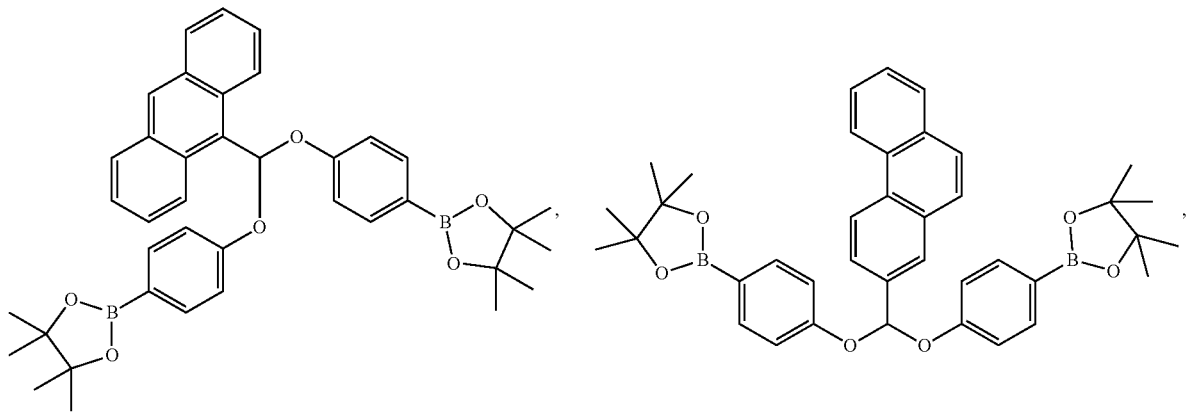
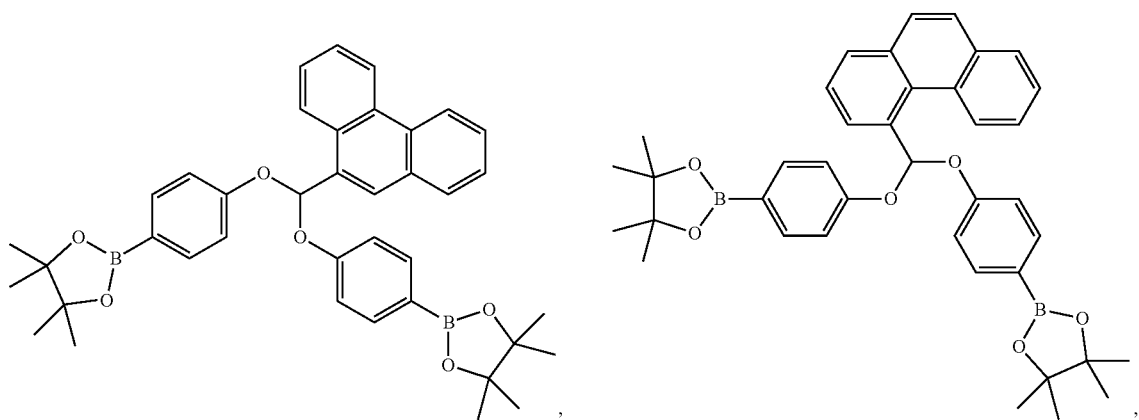
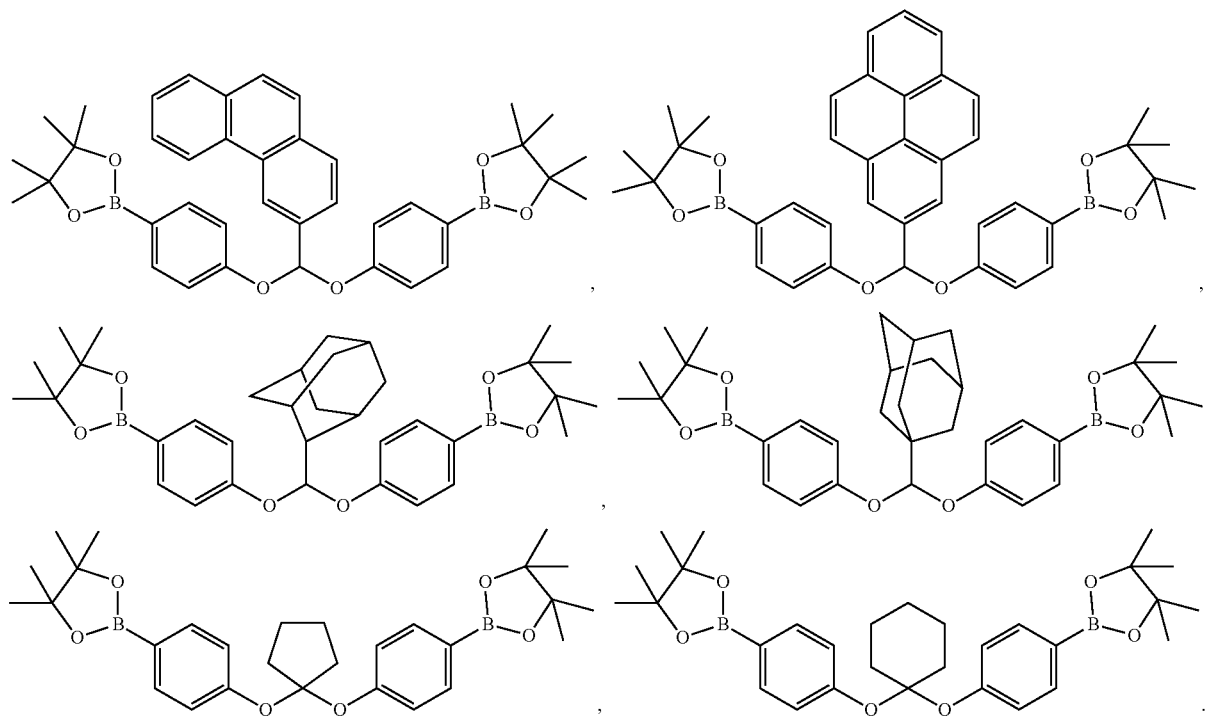

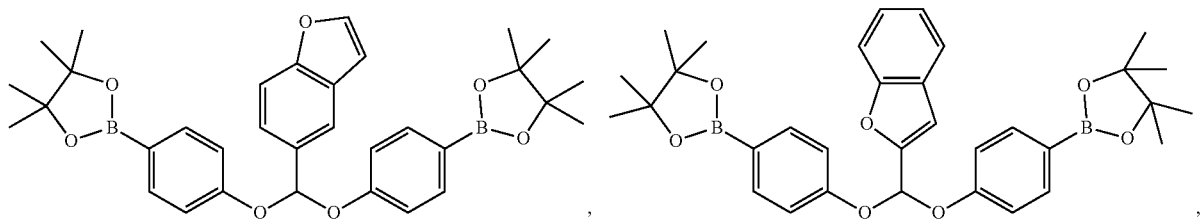
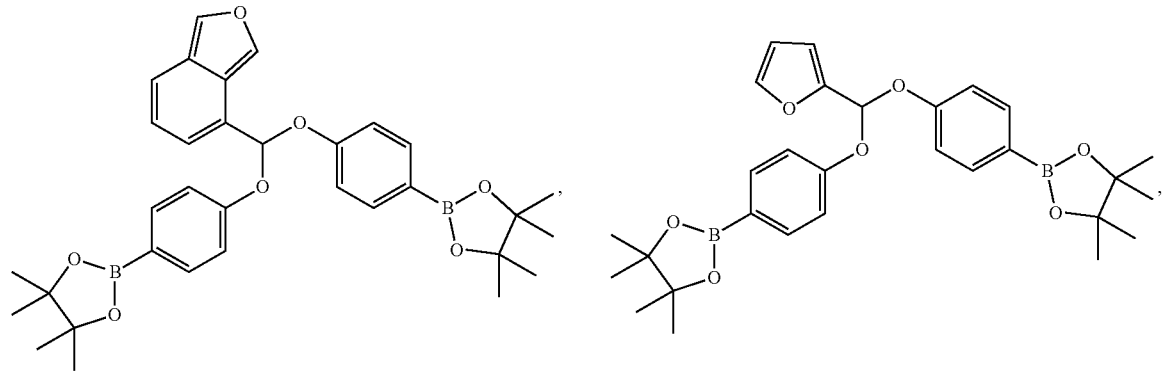
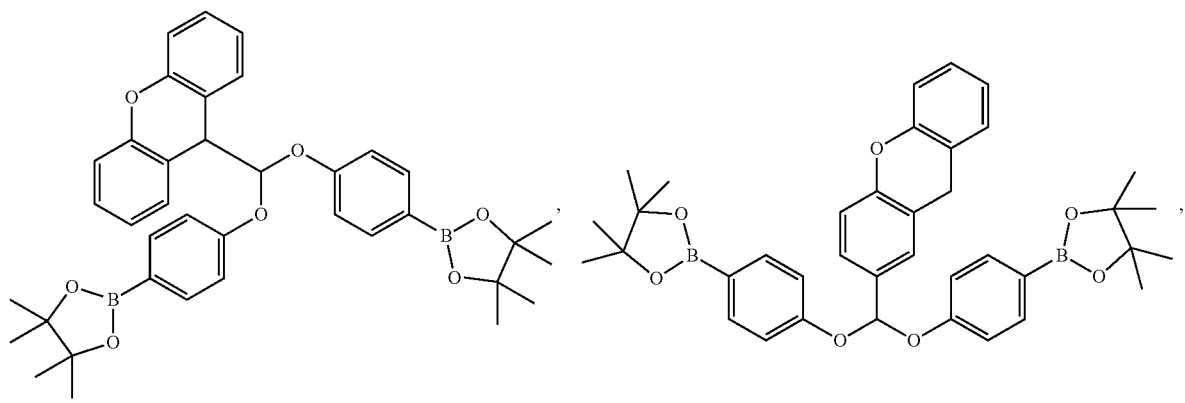
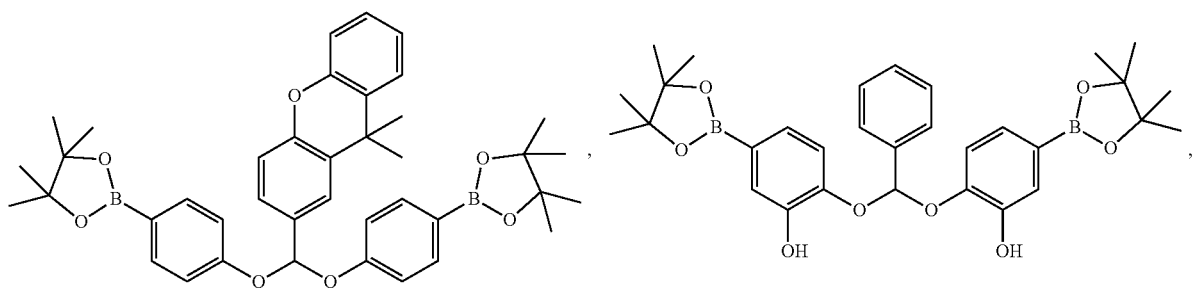
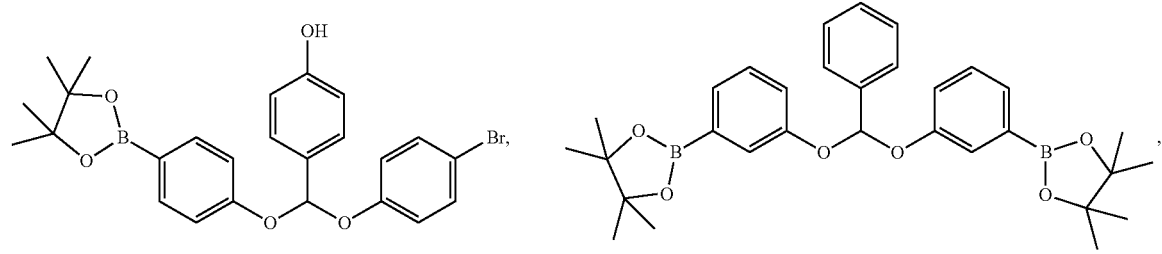

-continued
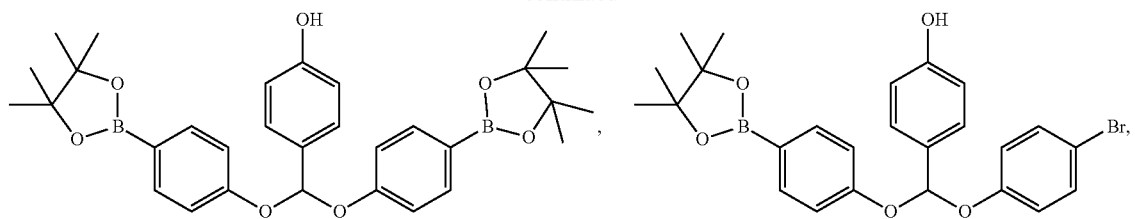
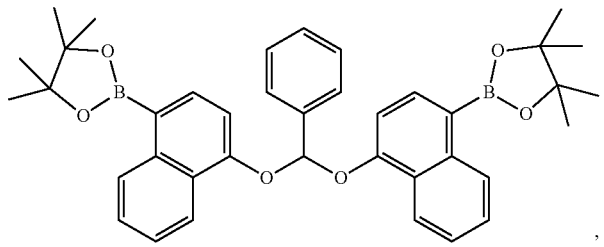
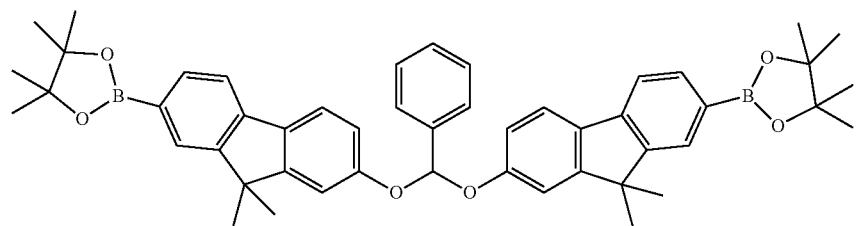
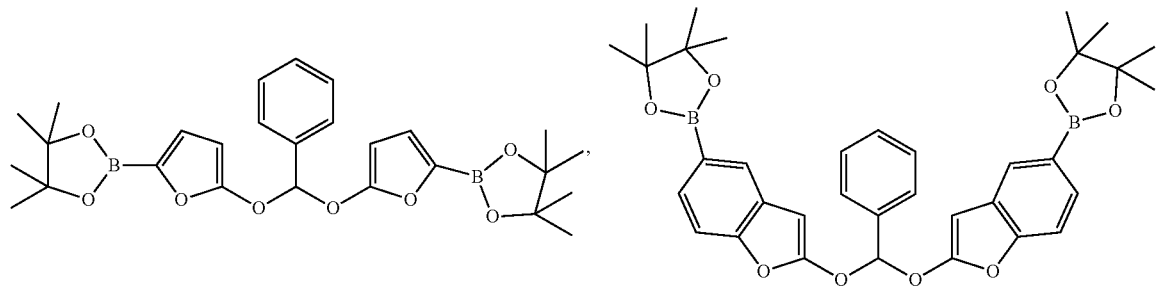
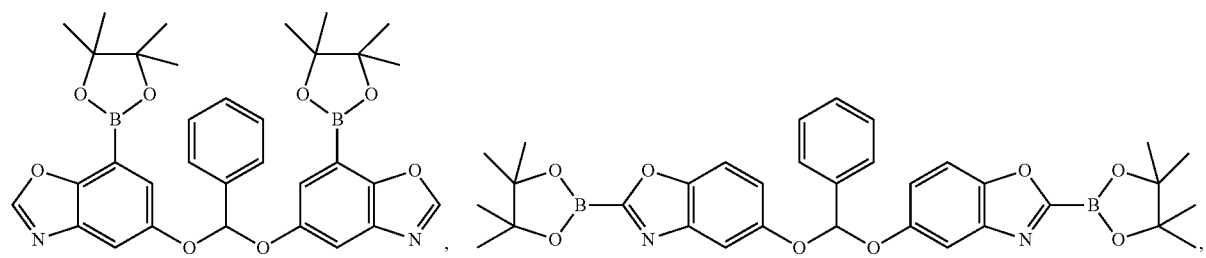
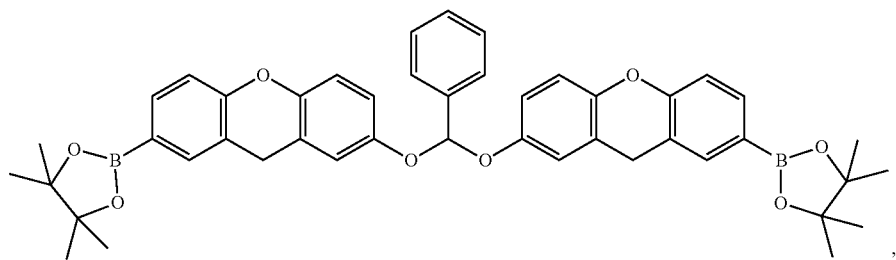

-continued
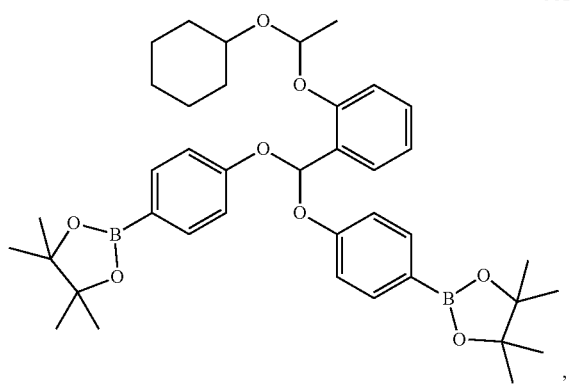
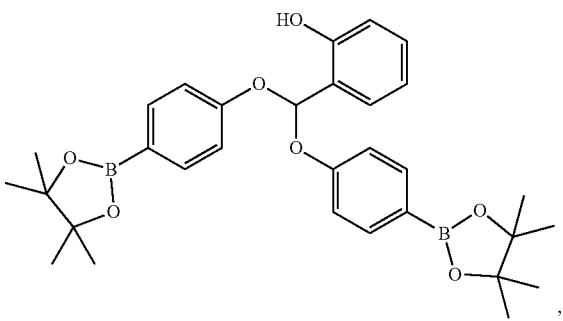
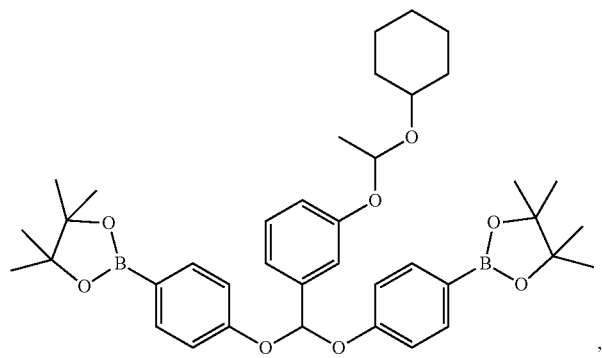
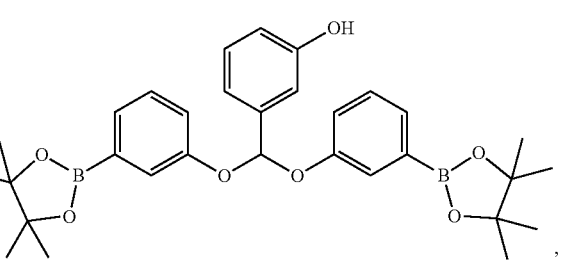
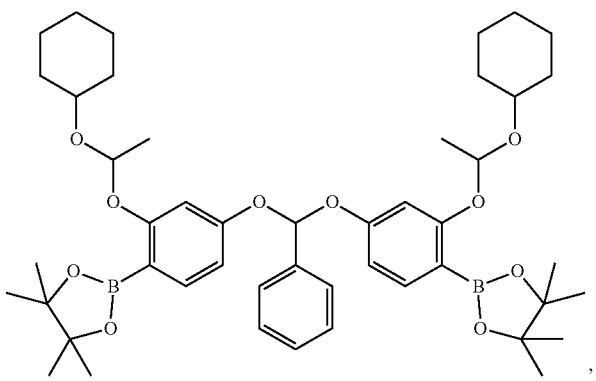
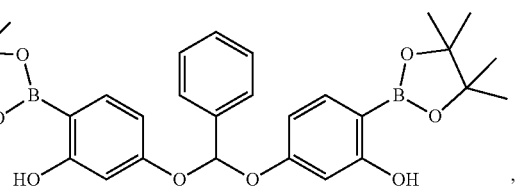
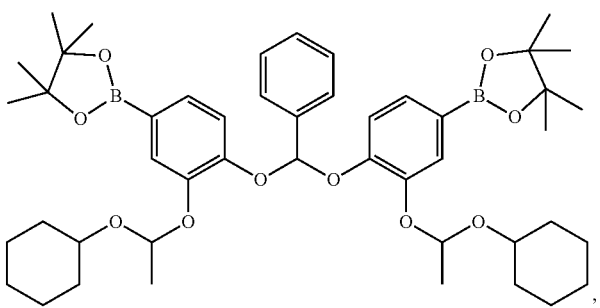
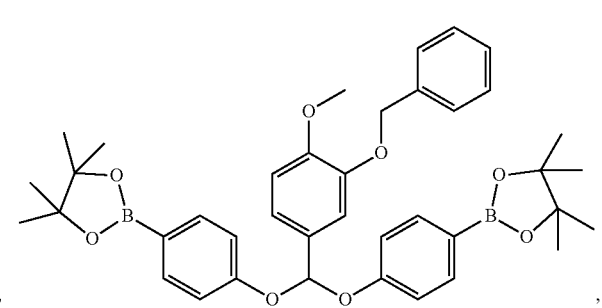
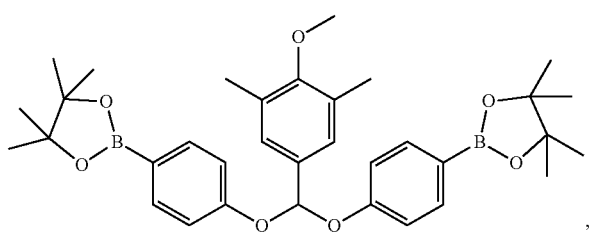
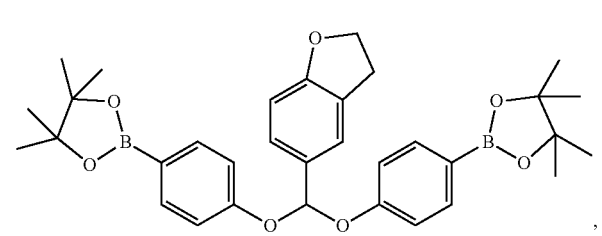

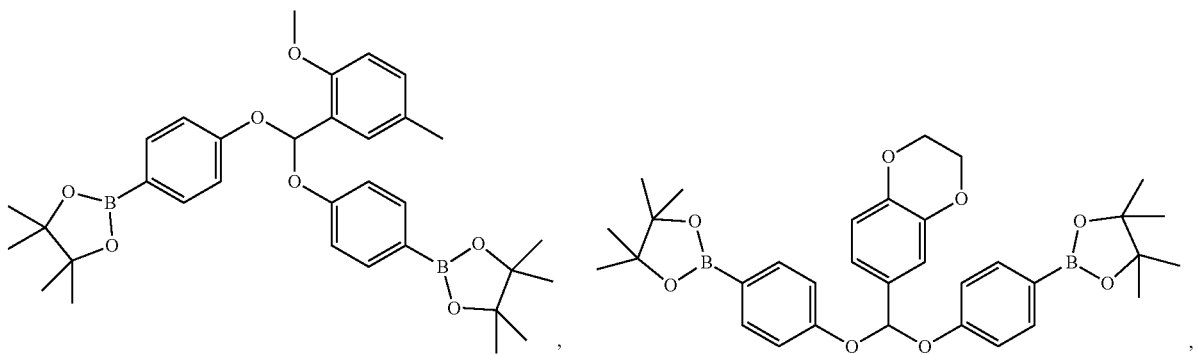
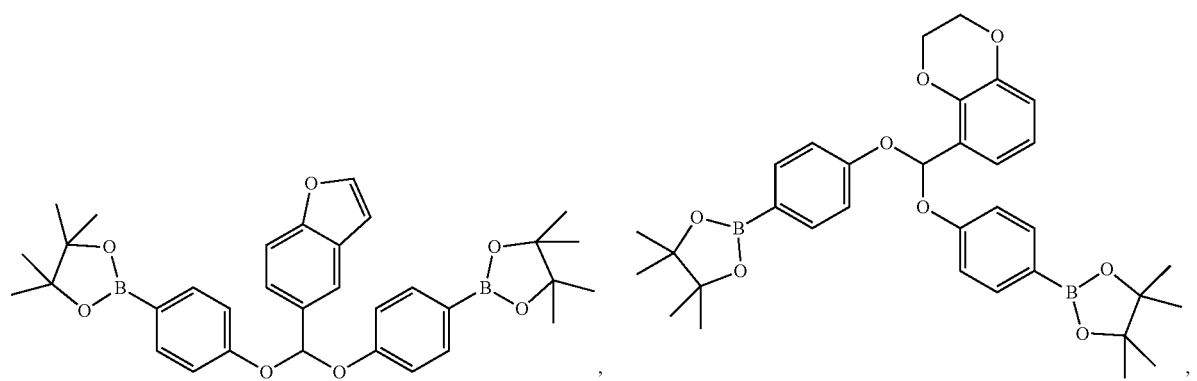
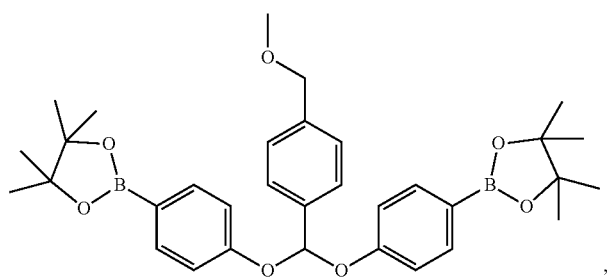
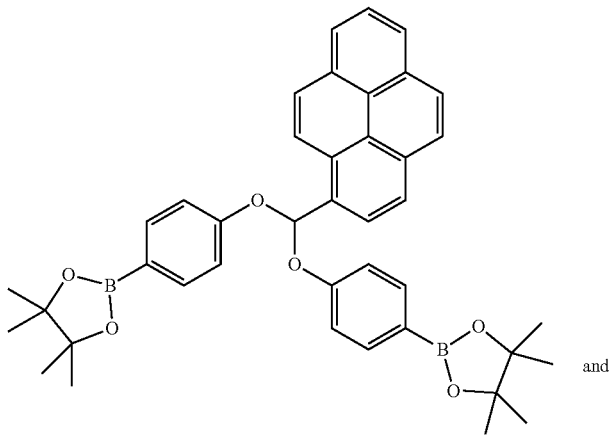
and

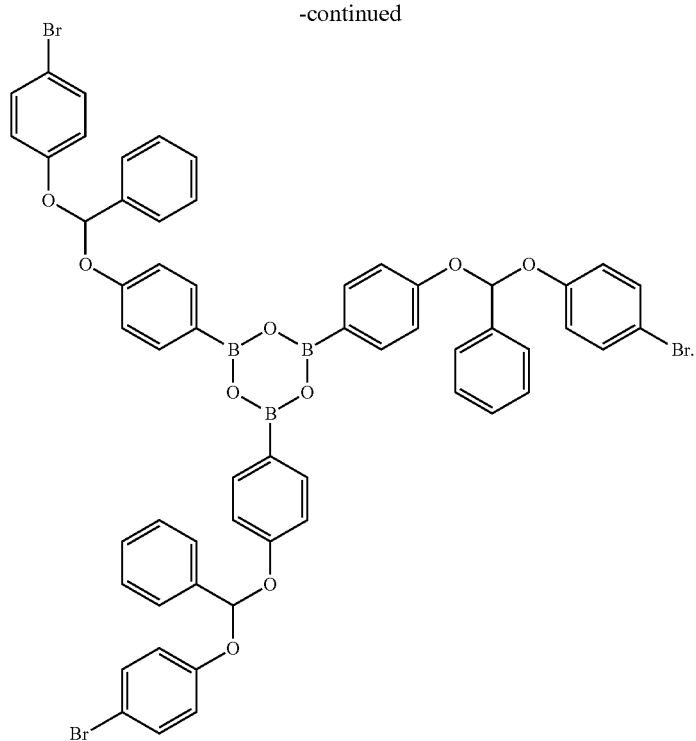
* * * * *